(12) United States Patent
Bak et al.

(10) Patent No.: US 7,009,088 B1
(45) Date of Patent: Mar. 7, 2006

(54) METHODS OF MODULATING AUXIN PRODUCTION IN PLANTS

(75) Inventors: Soren Bak, Copenhagen (DK); Kenneth A. Feldman, Newbury Park, CA (US); Rene Feyereisen, Valbonne (FR); Frans Tax, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 361 days.

(21) Appl. No.: 10/146,374

(22) Filed: May 13, 2002

Related U.S. Application Data

(63) Continuation of application No. 10/026,665, filed on Dec. 18, 2001, now abandoned.

(60) Provisional application No. 60/256,693, filed on Dec. 18, 2000, provisional application No. 60/317,374, filed on Sep. 4, 2001.

(51) Int. Cl.
  C12N 15/29 (2006.01)
  C12N 15/82 (2006.01)
  C12N 15/87 (2006.01)
  A01H 5/00 (2006.01)

(52) U.S. Cl. .................. 800/278; 800/298; 800/306; 800/287; 435/468

(58) Field of Classification Search ............... 800/298, 800/290, 278, 287, 306; 536/23.1; 435/468
See application file for complete search history.

(56) References Cited

U.S. PATENT DOCUMENTS

| | | | |
|---|---|---|---|
| 4,801,340 A | 1/1989 | Inoue et al. | |
| 5,034,323 A | 7/1991 | Jorgensen et al. | |
| 5,231,020 A | 7/1993 | Jorgensen et al. | |
| 5,283,184 A | 2/1994 | Jorgensen et al. | |
| 6,300,544 B1 | 10/2001 | Halkier et al. | |

OTHER PUBLICATIONS

Mizutani et al (1998, Plant Molecular Biology 37 :39-52).*
Hemm et al (2003, The Plant Cell 15:179-194).*
Bilodeau et al (Jul. 1999, Plant, Cell and Environment 22:791-800).*
Bak et al (2001, Plant Physiology 127:108-118).*
Naur et al., CYP83A1 and CYP83B1, Two Nonredundant Cytochrome P450 Enzymes Metabolizing Oximes in the Biosyntehsis of Glucosinolates in Arabidopsis, Plant Physiology, vol. 33, pp. 63-72 (Sep. 2003).
GenBank Accession No. 3164125 dated Feb. 14, 2004, Mizutani et al.
GenBank Accession No. 3164126 dated Feb. 14, 2004, Mizutani et al.
Adams et al., "Hindered dialkylamino nucleoside phosphite reagents in the synthesis of two DNA 51-mers," *J. Am. Chem. Soc.*, 1983, 105:661-663.
Andersen et al., "Cytochromes P-450 from Cassava (*Manihot esculenta* Crantz) Catalyzing the First Steps in the Biosynthesis of Cyanogenic Glucosides Linamarin and Lotaustralin," *J. Biol. Chem.*, 2000, 275:1966-1975.
Bak et al., "Cloning of three A-type cytochromes P450, CYP71E1, CYP98, and CYP99 from *Sorghum bicolor* (L.) Moench by a PCR approach and identification by expression in *Escherichia coli* of CYP71E1 as a multifunctional cytochrome P450 in the biosynthesis of the cyanogenic glucoside dhurrin," *Plant Mol. Biol.*, 1998, 36:393-405.
Bak et al., "The presence of CYP79 homologues in glucosinolate-producing plants shows evolutionary conservation of the enzymes in the conversion of amino acid to aldoxime in the biosynthesis of cyanogenic glucosides and glucosinolates," 1998, *Plant Mol. Biol.*, 38:725-734.
Bak and Feyereisen, "The Involvement of Two P450 Enzymes, CYP83B1 and CYP83A1, in Auxin Homeostasis and Glucosinolate Biosynthesis," *Plant Physiol.*, 2001, 127: 108-118.
Bak et al., "CYP83B1, a Cytochrome P450 at the Metabolic Branch Point in Auxin and Indole Glucosinolate Biosynthesis in Arabidopsis," *Plant Cell*, 2001, 13:101-111.
Bak et al., "Metabolic engineering of p-hydroxybenzylglucosinolate in *Arabidopsis* by expression of the cyanogenic CYP79A1 from *Sorghum bicolor*," *Plant J.*, 1999, 20:663-671.
Bartel and Fink, "Differential regulation of an auxin-producing nitrilase gene family in *Arabidopsis thaliana*," *Proc. Natl. Acad. Sci. USA*, 1994, 91:6649-6653.
Bartel, "Auxin Biosynthesis," *Ann. Rev. Plant Physiol. Plant Mol. Biol.*, 1997, 48:51-66.
Boulton et al., "Specificity of *Agrobacterium*-mediated delivery of maize streak virus DNA to members of the Gramineae," *Plant Mol. Biol.*, 1989, 12:31-40.
Brisson et al., "Expression of the bacterial gene in plants by using a viral vector," *Nature*, 1984, 310:511-514.
Bustos et al., "Regulation of β-Glucuronidase Expression in Transgenic Tobacco Plants by an A/T-Rich, cis-Acting Sequence Found Upstream of a French Bean β-Phaseolin Gene," *Plant Cell*, 1989, 1:839-854.
Chavadej et al., "Redirection of tryptophan leads to production of low indole glucosinolate canola," *Proc. Natl. Acad. Sci. USA*, 1994, 91:2166-2170.
Clark-Lewis et al., "Chemical Synthesis, Purification, and Characterization of Two Inflammatory Proteins, Neutrophil Activating Peptide 1 (Interleukin-8) and Neutrophil Activating Peptide 2," *Biochem.*, 1991, 30:3128-3135.

(Continued)

*Primary Examiner*—David T. Fox
*Assistant Examiner*—Stuart F. Baum
(74) *Attorney, Agent, or Firm*—Fish & Richardson P.C., P.A.

(57) ABSTRACT

The present invention relates to methods for modulating auxin and glucosinolate production in plants, specifically by modulating CYP83B1 expression. The present invention also relates to transgenic plants that overexpress and underexpress CYP83B1.

7 Claims, 7 Drawing Sheets

OTHER PUBLICATIONS

Creighton, *Proteins, Structures and Molecular Principles,* 1983, W.H. Freeman and Co., N.Y., pp. 34-49 and 50-60.

Davies, *Plant Hormones,* 1995, Kluwer Academic Publishers, Dordrecht, The Netherlands, pp. 1-12.

Dayhoff, *Atlas of Protein Sequences and Structure,* National Biomedical Research Foundation, Washington, D.C., 5 Suppl., 3:353-358.

Delarue et al., "Sur2 mutations of Arabidopsis thaliana define a new locus involved in the control of Auxin homeostasis," *Plant J.,* 1998, 14:603-611.

D'Halluin et al., "Transgenic Maize Plants by Tissue Electroporation," *Plant Cell,* 1992, 4:1495-1505.

Du et al., "Involvement of cytochrome P450 in oxime production in glucosinolate biosynthesis as demonstrated by an in vitro microsomal enzyme system isolated from jasmonic acid-induced seedlings of *Sinapsis alba* L.," *Proc. Natl. Acad. Sci. USA,* 1995, 92:12505-12509.

Feldmann, "Cytochrome P450s as genes for crop improvement," *Curr. Opin. Plant Biol.,* 2001, 4:162-167.

Gould et al., "Transformation of *Zea mays* L. Using *Agrobacterium tumefaciens* and the Shoot Apex," *Plant Physiol.,* 1991, 95:426-434.

Grsic et al., "Physiological Analysis of Transgenic *Arabidopsis thaliana* Plants Expressing one Nitrilase Isoform in Sense or Antisense Direction," *J. Plant Physiol.,* 1998, 153:446-456.

Grsic-Rausch et al., "Expression and Localization of Nitrilase during Symptom Development of the Clubroot Disease in Arabidopsis," *Plant Physiol.,* 2000, 122:369-378.

Guilfoyle et al., "How Does Auxin Turn On Genes?" *Plant Physiol.,* 1998, 118:341-347.

Hajdukiewicz et al., "The small, versatile pPZP family of *Agrobacterium* binary vectors for plant transformation," *Plant Mol. Biol.,* 1994, 25:989-994.

Halkier and Du, "The biosynthesis of glucosinolates," *Trends Plant Sci.,* 1997, 2:425-430.

Halkier et al., "Purification and Characterization of Recombinant Cytochrome $P450_{TYR}$ Expressed at High Levels in *Escherichia coli,*" *Arch. Biochem. Biophys.,* 1995, 322:369-377.

Halkier, "Glucosinolates," *Naturally Occurring Glycosides: Chemistry Distribution and Biological Properties,* 1999, Chapter 6, John Wiley & Sons Ltd., pps. 193-194, 213-223.

Higo et al., "Plant cis-acting regulatory DNA elements (PLACE) database:1999," *Nucl. Acids Res.,* 1999, 27:297-300.

Hull et al., "*Arabidopsis* Cytochrome P450s that catalyze the first step of tryptophan-dependent indole-3-acetic acid biosynthesis," *Proc. Natl. Acad. Sci. USA,* 2000, 97:2379-2384.

Kaeppler et al., "Silicon carbide fiber-mediated DNA delivery into plant cells," *Plant Cell Reports,* 1990, 9:415-418.

Mayer et al., "Sequence and analysis of chromosome 4 of the plant *Arabidopsis thaliana,*" *Nature,* 1999, 402:769-777.

Meier et al., "Elicitor-Inducible and Constitutive in Vivo DNA Footprints Indicate Novel cis-Acting Elements in the Promoter of a Parsley Gene Encoding Pathogenesis-Related Protein 1," *Plant Cell,* 1991, 3:309-316.

Mizutani et al., "Cytochrome p450 superfamily in *Arabidopsis thaliana:* isolation of CDNAs, Differential Expression, and RFLP mapping of multiple cytochromes P450," *Plant Mol. Biol.,* 1998, 37:39-52.

Müller et al., "Indole-3-acetic acid is synthesized from L-Tryptophan in roots of *Arabidopsis thaliana,*" *Planta,* 1998, 206:362-369.

Nielsen and Moller, "Cloning and Expression of Cytochrome P450 Enzymes Catalyzing the Conversion of Tyrosine to p-Hydroxyphenylacetaldoxime in the Biosynthesis of Cyanogenic Glucosides in *Triglochin maritima,*" *Plant Physiol.,* 2000, 122:1311-1321.

Normanly and Bartel, "Redundancy as a way of life—IAA metabolism," *Curr. Opin. Plant Biol.,* 1999, 2:207-213.

Normanly et al., "Arabidopsis Mutants Resistant to the Auxin Effects of Indole-3-Acetonitrile Are Defective in the Nitrilase Encoded by the *NIT1* Gene," *Plant Cell,* 1997, 9:1781-1790.

Normanly et al., "*Arabidopsis thaliana* auxotrophs reveal a tryptophan-independent biosynthetic pathway for indole-3-acetic acid," *Proc. Natl. Acad. Sci. USA,* 1993, 90:10355-10359.

Paquette et al., "Intron-Exon Organization and Phylogeny in a Large Superfamily, the Paralogous Cytochrome P450 Genes of *Arabidopsis thaliana,*" *DNA Cell Biol.,* 2000, 19:307-317.

Pompon et al., "Yeast Expression of Animal and Plant P450s in Optimized Redox Environments," *Methods Enzymol.,* 1996, 272:51-64.

Poulton and Møller, "Glucosinolates," *Meth. Plant Biochem.,* 1993, 9:209-237.

Selmar, "Biochemistry of Plant Secondary Metabolism," *Ann. Plant Rev.,* 1999, 2:79-150.

Seo et al., "Higher Activity of an Aldehyde Oxidase in the Auxin-Overproducing *superroot1* Mutant of *Arabidopsis thaliana,*" *Plant Physiol.,* 1998, 116:686-693.

Smith and Waterman, "Comparison of Biosequences," *Adv. Appl. Math.,* 1981, 2:482-489.

Tatersall, "Resistance to an Herbivore Through Engineering Cyanogenic Glucoside Synthesis," *Science,* 2001, 293:1826-1828.

Ulmasov et al., "Dimerization and DNA binding of auxin response factors," *Plant J.,* 1999, 19:309-319.

Wildman, "The auxin-A, B enigma: scientific fraud or scientific ineptitude?" *Plant Growth Reg.,* 1997, 23:37-68.

Winkler et al., "Systematic Reverse Genetics of Transfer-DNA-Tagged Lines of Arabidopsis," *Plant Physiol.,* 1998, 118:743-750.

Wittstock and Halkier, "Cytochrome P450 CYP79A2 from *Arabidopsis thaliana* L. Catalyzes the Conversion of L-Phenylalanine to Phenylacetaldoxime in the Biosynthesis of Benzylglucosinolate," *J. Biol. Chem.,* 2000, 275:14659-14666.

Zhang et al., "DNA Sequences That Activate Isocitrate Lyase Gene Expressing during Late Embryogenesis and during Postgerminative Growth," *Plant Physiol.,* 1996, 110-1069-1079.

Zhou et al., "Arabidopsis *PAD3,* a Gene Required for Camalexin Biosynthesis, Encodes a Putative Cytochrome P450 Monooxygenase," *Plant Cell,* 1999, 11:2419-2428.

* cited by examiner

```
   1 gtcaaacaga aaaaaatgga tctcttattg attatagccg gtttagtagc ggctgcagcc
  61 ttcttttcc  tccgtagcac gaccaagaaa tctctccggt tacctccggg accaaaaggt
 121 cttcctatta taggaaacct tcaccagatg gagaaattca accccccaaca cttccttttc
 181 cgtctctcca agctatacgg cccgattttc acgatgaaaa tcggtggccg tcgcctcgcg
 241 gtgatctcct cggccgagct agccaaggag ctactcaaaa ctcaagacct caacttcacc
 301 gctcgtcctc tcttgaaagg gcaacaaacc atgtcgtatc aaggccgtga gcttggtttc
 361 ggacagtaca ccgcgtacta ccgtgagatg aggaagatgt gtatggtgaa cctcttcagc
 421 ccgaaccgtg tcgcaagttt cagaccggtt agagaagaag agtgtcaacg gatgatggac
 481 aagatctata aagccgctga tcaatcaggc accgttgatc taagtgagct tctcttgtct
 541 ttcactaact gtgtcgtatg tagacaagct tttgggaaac ggtacaatga gtacggcaca
 601 gagatgaaga gattcataga tatcttgtac gagacgcaag cacttttggg cactctgttt
 661 ttctccgacc ttttcccta  tttcggattc cttgacaacc tcactggtct cagtgcacgt
 721 ctcaagaaag ctttcaagga gcttgacact taccttcaag aacttctaga cgagactctt
 781 gaccctaacc gccctaaaca agaaacagag agtttcattg atcttttgat gcagatctac
 841 aaagaccaac ctttctccat caaattcact cacgaaaatg tcaaggccat gatattggat
 901 attgttgtgc cgggaactga cacggcggct gcagtggtgg tatgggccat gacttacctt
 961 attaagtacc ctgaagcaat gaagaaagct caagacgaag tgaggagtgt gataggtgac
1021 aaaggatatg tctctgaaga agacataacct aatctcccctt acctaaaggc agtcatcaag
1081 gagtctcttc ggctcgaacc agtcatcccc attcttctac acagagaaac tatcgcagac
1141 gcaaagatag gtggctatga tattccggcc aagaccatca ttcaggtgaa cgcatgggcg
1201 gtttctcgtg acacagccgc gtggggagac aaccctaatg agttcattcc agagaggttc
1261 atgaacgagc acaaaggagt ggacttcaag ggccaagatt ttgagctcct acctttcggg
1321 tcgggccgga gaatgtgccc ggccatgcat cttgggattg caatggtaga gatacctttc
1381 gctaaccttc tctacaaatt tgactggagt ctacctaaag ggattaaacc agagggatata
1441 aagatggacg tcatgactgg actcgctatg cacaagaaag aacacctcgt tcttgcacca
1501 acgaaacaca tctgatgcta tatatatcat taggacgttt ctgctggtag atatggcgtg
1561 accaatggtt atttttcatt gcaatatccc tttttgtttt aatgagtact atgttctcat
1621 tttaacgaat aaaaatgtat cagtgctctt gtttttggac tag (SEQ ID NO:1)
```

FIG. 1

```
  1  mdllliiagl  vaaaaffflr  sttkkslrlp  pgpkglpiig  nlhqmekfnp  qhflfrlskl
 61  ygpiftmkig  grrlavissa  elakellktq  dlnftarpll  kgqqtmsyqg  relgfgqyta
121  yyremrkmcm  vnlfspnrva  sfrpvreeec  qrmmdkiyka  adqsgtvdls  elllsftncv
181  vcrqafgkry  neygtemkrf  idilyetqal  lgtlffsdlf  pyfgfldnlt  glsarlkkaf
241  keldtylqel  ldetldpnrp  kqetesfidl  lmqiykdqpf  sikfthenvk  amildivvpg
301  tdtaaavvvw  amtylikype  amkkaqdevr  svigdkgyvs  eedipnlpyl  kavikeslrl
361  epvipillhr  etiadakigg  ydipaktiiq  vnawavsrdt  aawgdnpnef  iperfmnehk
421  gvdfkgqdfe  llpfgsgrrm  cpamhlgiam  veipfanlly  kfdwslpkgi  kpedikmdvm
481  tglamhkkeh  lvlaptkhi   (SEQ ID NO:2)
```

FIG. 2

METHODS OF MODULATING AUXIN PRODUCTION IN PLANTS

CROSS-REFERENCE TO RELATED APPLICATIONS

This application claims, is a CON of and priority to U.S. application Ser. No. 10/026,665, filed Dec. 18, 2001, abandoned, which claims priority under 35 U.S.C. §119(e)(1) to provisional patent application Ser. Nos. 60/256,693, filed Dec. 18, 2000, and 60/317,374, filed Sep. 4, 2001, which applications are incorporated herein by reference in their entireties.

TECHNICAL FIELD

The present invention relates to novel methods of regulating plant phenotypes. In particular, the invention relates to methods of modulating auxin and glucosinolate production by overexpressing or underexpressing CYP83B1.

BACKGROUND

Auxins are growth regulators involved in virtually all aspects of plant development. For example, apical dominance, cell expansion, vascular differentiation, lateral root and root hair formation, phototropism and root gravitropism are among the many processes in plants controlled by auxins (DAVIES P. J. (1995) In *Plant Hormones* Kluwer Academic Publishers, Dordrecht, The Netherlands, pp 1–12). The level of auxin is regulated by both de novo biosynthesis and reversible and irreversible conjugation to sugars, amino acids and peptides as well as by degradation. Though the chemical structure of the primary auxin, indole-3-acetic acid (IAA), has been known since the 1930's (Wildman S. G. (1997) *Plant Growth Reg.* 23:37–68) not much is known about how plants actually synthesize this essential compound. Plants appear to be capable of synthesizing IAA by both tryptophan-dependent and tryptophan-independent pathways. Classical incorporation studies with radiolabeled compounds have not unambiguously identified either the precursors nor elucidated the biosynthetic pathway for IAA. (For a recent review on IAA metabolism, see Normanly and Bartel (1999) *Curr. Opin. Plant Biol.* 2:207–213.)

Although a number of mutants in IAA metabolic pathways and perception have been described, the genes involved and their biochemical function and physiological relevance have not all been elucidated (reviewed in Bartel B. (1997) *Ann. Rev. Plant Physiol. Plant Mol. Biol.* 48:51–66; Normanly and Bartel (1999) *Curr. Opin. Plant Biol.* 2:207–213). For example, the rty/surl/hls3/alfl and sur2 mutants are both known to accumulate increased levels of free auxin. Identification of the proteins or gene products affected and elucidation of the biochemical roles of these genes/proteins should increase the limited knowledge of IAA biosynthesis and regulation.

Glucosinolates are sulfur containing bioactive natural products derived from amino acids and sequestered in vacuoles of cruciferous plants (Selmar (1999) In *Biochemistry of Plant Secondary Metabolism. Annual Plant Reviews* 2:79–150). It has recently been shown that the cytochromes CYP79B2 and CYP79B3 of *Arabidopsis thaliana* both metabolize tryptophan to indole-3-acetaldoxime. This metabolite has been suggested to be the precursor of indole-3-acetonitrile (IAN) in IAA biosynthesis (Normanly and Bartel (1999) *Curr. Opin. Plant Biol.* 2:207–213; Hull et al. (2000) *Proc. Natl. Acad. Sci. USA* 97:2379–2384), as well as of thiohydroximates in glucosinolate biosynthesis, though neither step has been characterized biochemically. Nitrilases that catalyze the conversion of IAN to IAA are well characterized in *Arabidopsis* (Bartel and Fink (1994) *Proc. Natl. Acad. Sci. USA* 91:6649–6653). In this species, four differentially regulated nitrilases have been identified, though their physiological role is not clear (Normanly and Bartel (1999) *Curr. Opin. Plant Biol.* 2:207–213). A mutation for one of the nitrilase genes, nit1, renders *Arabidopsis* seedlings insensitive to exogenously applied IAN, yet this mutant does not have an apparent physiological IAA phenotype under normal conditions. (Normanly et al. (1993) *Proc. Natl. Acad. Sci. USA* 90:10355–10359).

Thus, there remains a need for the identification and characterization of enzymes that regulate auxin and glucosinolate synthesis.

SUMMARY OF THE INVENTION

The present invention is based on the discovery that a cytochrome P450, CYP83B1, is a regulator of auxin and glucosinolate production in *Arabidopsis*. Knockout of CYP83B1 leads to plants characterized by phenotypes including severe apical dominance. Conversely, overexpression of CYP83B1 leads to plants with decreased apical dominance. In addition, as demonstrated herein, CYP83B1 catalyzes the first committed step in indole glucosinolate biosynthesis by metabolizing indole-3-acetaldoxime to its aci-nitro compounds which leads to N-alkylthiohydroximates, the committed precursors of glucosinolates. Not only is the first part of IAA and of indole glucosinolate biosynthesis shared, but indole glucosinolates may function as a regulatory sink for IAA. Furthermore, the phylogenetic relationship between CYP83B1 and CYP71E1, the cytochrome P450 involved in the oxime-metabolizing step in cyanogenic glucoside biosynthesis, evidences an evolutionary relationship between IAA, glucosinolate and cyanogenic glucoside biosynthesis.

Accordingly, in one aspect, the present invention includes a transgenic plant that displays an altered auxin phenotype relative to the wild-type plant. In another embodiment, the transgenic plant has altered CYP83B1 expression.

In another aspect, the invention includes a method of producing a transgenic plant with altered CYP83B1 expression relative to the wild-type plant. The method comprises the steps of (a) introducing an expression construct described herein into a plant cell to produce a transformed plant cell, wherein the expression construct comprises a polynucleotide encoding a CYP83B1 polypeptide operably linked to a promoter which is capable of overexpressing or underexpressing the polypeptide; and (b) producing a transgenic plant from the transformed plant cell with altered CYP83B1 expression. In certain embodiments, at least one polynucleotide is operably linked to a promoter selected from the group consisting of a tissue-specific promoter, an inducible promoter and a constitutive promoter. The polypeptide can be overexpressed, underexpressed, or it can inhibit expression of CYP83B1. In a still further embodiment, at least two polynucleotides are introduced into the plant cell. Each polynucleotide is operably linked to a different tissue-specific promoter such that one polynucleotide is overexpressed while the other inhibits expression of CYP83B1.

In another embodiment, the invention relates to a method of producing a transgenic plant with altered CYP83B1 expression relative to the wild-type plant. The method comprises: (a) introducing a polynucleotide that inhibits expression of a CYP83B1 polynucleotide into a plant cell to produce a transformed plant cell; and (b) producing a transgenic plant from the transformed plant cell with altered CYP83B1 expression.

The altered phenotype due to CYP83B1 over- or under-expression includes altered morphological appearance and altered biochemical activity, for example, altered (reduced or increased) cell length in any cell or tissue, altered (extended or decreased) periods of flowering, altered (increased or decreased) branching, altered (increased or decreased) seed production, altered (increased or decreased) leaf size, altered (elongated or shortened) hypocotyls, altered (increased or decreased) plant height, altered cytochrome P450 activity, altered heme-thiolate enzyme activity, altered CYP83B1 expression (under- or overexpressed), regulation of auxin synthesis and altered resistance to plant pathogens.

In yet another aspect, the invention includes a method for altering the biochemical activity of a cell comprising the following steps: introducing an expression construct described herein into a plant cell to produce a transformed plant cell, wherein the expression construct comprises a polynucleotide encoding a CYP83B1 polypeptide operably linked to a promoter which is capable of overexpressing or underexpressing the polypeptide; and growing the cell under conditions such that the biochemical activity of the cell is altered. Biochemical activity includes, for example, altered CYP83B1 enzyme activity and regulation of auxins. In certain embodiments, the expression construct is introduced ex vivo. In other embodiments, the expression construct is provided to the cell in vivo. In still other embodiments, more than one expression construct is provided to the cell.

In yet another aspect, the invention includes a method for regulating the cell cycle of a plant cell comprising the following steps: providing a polynucleotide as described herein to a plant cell; and expressing the polynucleotide to provide the encoded polypeptide, wherein the polypeptide is provided in amounts such that cell cycling is regulated. In certain embodiments, the plant cell is provided in vitro and is cultured under conditions suitable for providing the polypeptide. In still other embodiments, the polynucleotide is provided in vivo.

In another aspect, the invention includes a method for producing a transgenic plant with altered expression of a cytochrome P450 that catalyzes the conversion of indole-3-acetaldoxime to a corresponding aci-nitro and the conversion of the aci-nitro to a corresponding S-alkyl-thiohydroximate and the conversion of the S-alkyl-thiohydroximate to indole glucosinolate, the method comprising introducing an expression construct that comprises a polynucleotide encoding a cytochrome P450 polypeptide operably linked to a promoter which is capable of overexpressing or underexpressing the polynucleotide, into a plant cell to produce a transformed plant cell, and producing a transgenic plant from the transformed plant cell with altered cytochrome P450 expression. In certain embodiments, the cytochrome P450 is CYP83B1, and in other embodiments, the polynucleotide encoding a cytochrome P450 polypeptide is operably linked to a promoter selected from the group consisting of a tissue-specific promoter, an inducible promoter and a constitutive promoter.

In another aspect, the invention includes a method for producing a cytochrome P450 that catalyzes the conversion of indole-3-acetaldoxime to indole glucosinolate, the method comprising introducing an expression construct that comprises a polynucleotide encoding a cytochrome P450 polypeptide operably linked to a promoter which is capable of overexpressing or underexpressing the polypeptide, into a host cell to produce a transformed host cell, expressing the cytochrome P450 in the transformed host cell, and isolating the expressed cytochrome P450. In certain embodiments, the cytochrome P450 is CYP83B1. In yet other embodiments, the polynucleotide is operably linked to a promoter selected from the group consisting of a tissue-specific promoter, an inducible promoter and a constitutive promoter. The indole-3-acetaldoxime may be obtained from a tryptophan. The method further provides a method of producing an indole glucosinolate, the method comprising contacting indole-3-acetaldoxime with the cytochrome P450.

In another aspect, the invention includes a method for producing an indole glucosinolate, the method comprising contacting indole-3-acetaldoxime with a cytochrome P450, and isolating the indole glucosinolate. In certain embodiments, the cytochrome P450 is CYP83B1. In other embodiments, the cytochrome P450 is overexpressed in a transformed host cell. The transformed host cell comprises an expression construct that comprises a polynucleotide encoding a cytochrome P450 polypeptide operably linked to a promoter which is capable of overexpressing the polypeptide. The polynucleotide can be operably linked to a promoter selected from the group consisting of a tissue-specific promoter, an inducible promoter and a constitutive promoter. The indole-3-acetaldoxime can be obtained from a tryptophan.

In yet another aspect, the invention includes a method for producing an indole-3-acetic acid, the method comprising contacting indole-3-acetaldoxime with a transformed host cell underexpressing a cytochrome P450, and isolating the indole-3-acetic acid. The indole-3-acetaldoxime can be obtained from a tryptophan. In some embodiments, the cytochrome P450 is CYP83B1. In yet other embodiments, the transformed host cell comprises an expression construct that comprises a polynucleotide encoding a cytochrome P450 polypeptide operably linked to a promoter which is capable of underexpressing the polypeptide. The polynucleotide can be operably linked to a promoter selected from the group consisting of a tissue-specific promoter, an inducible promoter and a constitutive promoter.

In yet another aspect, the invention provides a method for producing indole-3-acetic acid, the method comprising contacting indole-3-acetaldoxime with a transformed host cell comprising an expression construct that comprises a polynucleotide encoding a cytochrome P450 polypeptide operably linked to a promoter which is capable of overexpressing or underexpressing the polypeptide, wherein the polynucleotide is linked to the promoter in the antisense orientation, and isolating the indole-3-acetic acid. In certain embodiments, the cytochrome P450 is CYP83B1. In other embodiments, the polynucleotide is operably linked to a promoter selected from the group consisting of a tissue-specific promoter, an inducible promoter and a constitutive promoter. The indole-3-acetaldoxime can be obtained from a tryptophan.

Any of the polynucleotides or polypeptides described herein can be used in diagnostic assays; to generate antibodies. Further, the antibodies and fragments thereof can also be used in diagnostic assays, to produce immunogenic compositions or the like.

These and other objects, aspects, embodiments and advantages of the present invention will readily occur to those of ordinary skill in the art in view of the disclosure herein.

BRIEF DESCRIPTION OF THE DRAWINGS

FIG. 1 depicts the nucleotide sequence (SEQ ID NO: 1) of native CYP83B1 (GenBank Accession No. 3164125).

FIG. 2 depicts the amino acid sequence (SEQ ID NO:2) of native CYP83B1 (GenBank Accession No. 3164126).

DETAILED DESCRIPTION

Figure 3:
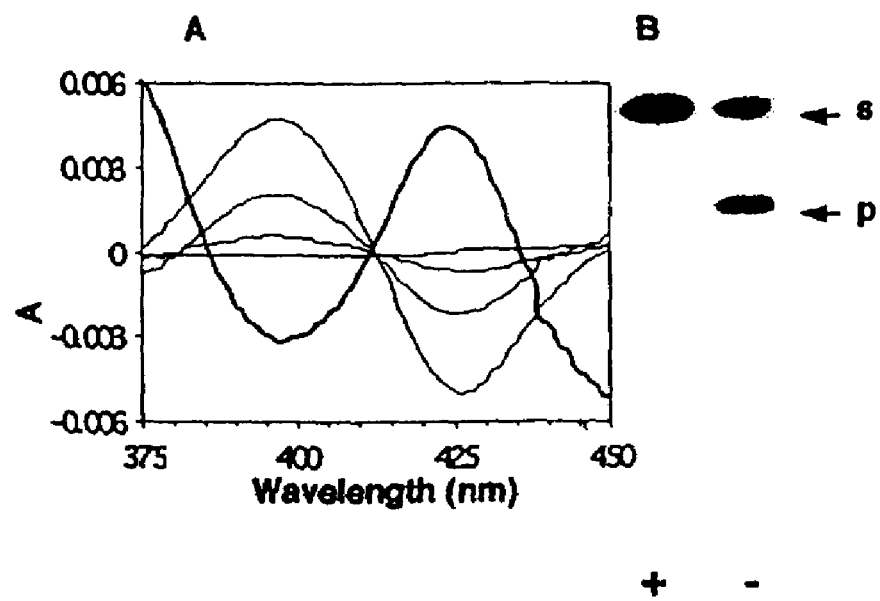
FIG. 3. (A) Analysis of CYP83B1 by optical difference spectroscopy. A saturated type Ia spectrum was obtained with 100 μM tryptamine, (thick line, trough at 390 nm, peak at 425 nm) in the sample cuvette. Addition of 100 μM tryptamine to both cuvettes gave a baseline. The increasing concentrations of indole-3-acetaldoxime in the sample cuvette (0.2 μM, 0.8 μM, 3.0 μM) then displaced tryptamine giving the reverse type IIa spectrum. (B) Tryptamine is an inhibitor of CYP83B1 catalysis. 22 nM CYP83B1 was incubated with 35 μM [5-$^3$H]indole-3-acetaldoxime in the absence (−) or presence (+) of 17.5 mM tryptamine. After incubation for 10 min at 28° C. reaction mixtures were extracted with ethylacetate and analyzed by TLC. (s) substrate, (p) product.

The present inventors have shown that CYP83B1 is a cytochrome P450 that regulates indole-3-acetic acid ("IAA" or "auxin") production from tryptophan in *Arabidopsis*. As shown in the examples, a T-DNA insertion in the CYP83B1 gene leads to plants with a phenotype characteristic of severe auxin overproduction, whereas CYP83B1 overexpression leads to loss of apical dominance typical of an auxin deficit. CYP83B1 metabolizes indole 3-acetaldoxime to the corresponding aci-nitro compound, with a $K_m$ of 3 μM and a turnover number of 53 min$^{-1}$. The aci-nitro compounds convert to N-alkylthiohydroximate adducts, the committed precursors of glucosinolates. Thus, indole-3-acetaldoxime is the metabolic branch point between the primary auxin indole-3 -acetic acid and indole glucosinolate biosynthesis in *Arabidopsis*. Accordingly, the present invention represents an important discovery in understanding and regulating plant cell growth.

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of plant biology, virology, microbiology, molecular biology, recombinant DNA techniques and immunology all of which are within the ordinary skill of the art. Such techniques are explained fully in the literature. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

Definitions

In describing the present invention, the following terms will be employed, and are intended to be defined as indicated below.

The terms "nucleic acid molecule" and "polynucleotide" are used interchangeably and refer to a polymeric form of nucleotides of any length, either deoxyribonucleotides or ribonucleotides, or analogs thereof. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides may have any three-dimensional structure, and may perform any function, known or unknown. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 43%–60%, preferably 60–70%, more preferably 70%–85%, more preferably at least about 85%–90%, more preferably at least about 90%–95%, and most preferably at least about 95%–98% sequence identity over a defined length of the molecules, or any percentage between the above-specified ranges, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids, wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), tissue-specific promoters (where expression of a polynucleotide sequence operably linked to the promoter is induced only in selected tissue), repressible promoters (where expression of a polynucleotide sequence operably linked to the promoter is induced by an analyte, cofactor, regulatory protein, etc.), and constitutive promoters.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagarno sequences).

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous sequence" as used herein typically refers to a nucleic acid sequence that is not normally found in the cell or organism of interest. For example, a DNA sequence encoding a polypeptide can be obtained from a plant cell and introduced into a bacterial cell. In this case the plant DNA sequence is "heterologous" to the native DNA of the bacterial cell.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

By "vector" is meant any genetic element, such as a plasmid, phage, transposon, cosmid, chromosome, virus etc., which is capable of transferring gene sequences to target cells. Generally, a vector is capable of replication when associated with the proper control elements. Thus, the term includes cloning and expression vehicles, as well as viral vectors and integrating vectors.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells, either in vivo or in vitro. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A cell has been "transformed" by an exogenous polynucleotide when the polynucleotide has been introduced inside the cell. The exogenous polynucleotide may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Figure 7:
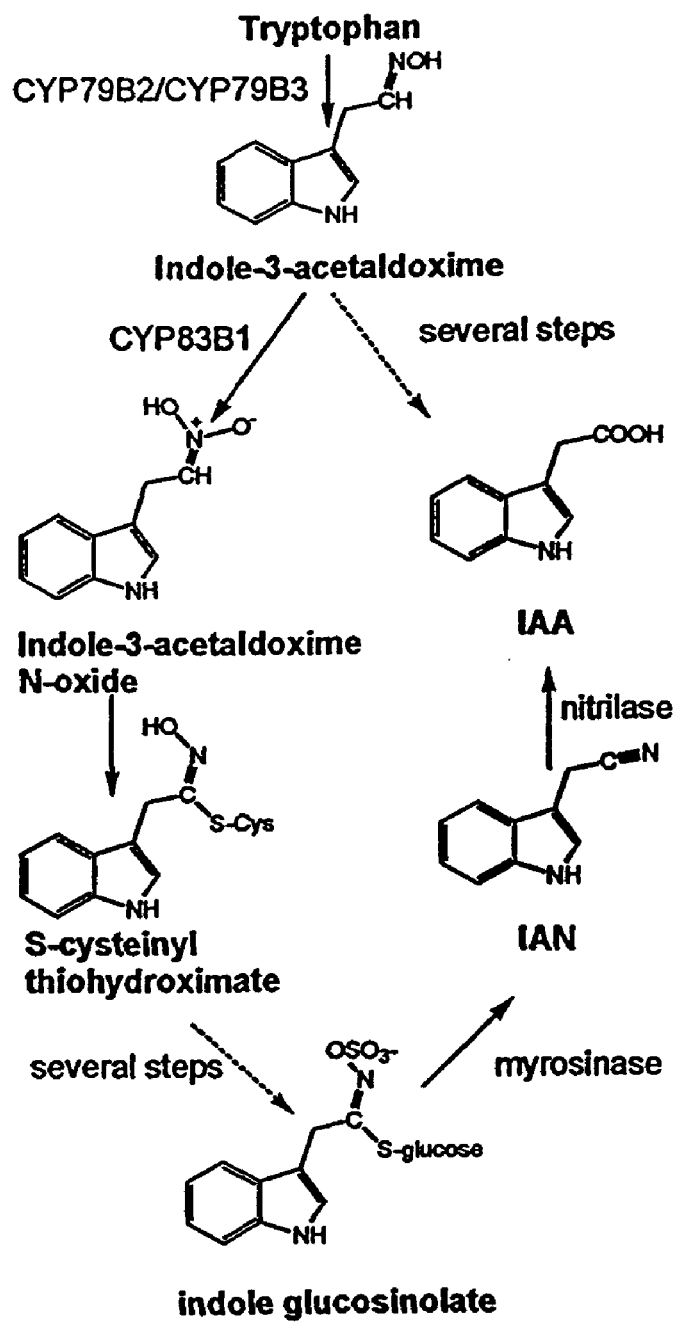
FIG. 7. Indole-3-acetaldoxime is the metabolic branch point to indole glucosinolates in IAA biosynthesis. In rntl-1 the pathway into indole glucosinolates through CYP83B1 is blocked leading to accumulation of IAA and plants with high IAA phenotype. Conversely, in CYP83B1 overexpression lines, additional indole-3-acetaldoxime is channeled into indole glucosinolate biosynthesis leading to plants with a low IAA phenotype and increased indole glucosinolate levels.

The term "CYP83B1 polynucleotide" refers to a polynucleotide derived from the gene encoding the CYP83B1 polypeptide that encodes a polynucleotide that retains CYP83B1 enzymatic activity. CYP83B1 is a cytochrome P450 that is a regulator of auxin production in *Arabidopsis* by controlling the flux of indole-3-acetaidoxime into IAA and indole glucosinolate biosynthesis. In addition, as shown herein, CYP83B1 catalyzes the first committed step in indole glucosinolate biosynthesis by metabolizing indole-3-acetaldoxime to its S-alkylthiohydroximate (see, FIG. 7). The CYP83B1 polynucleotide sequence and corresponding amino acid sequence are shown in FIGS. 1 and 2, respectively (GenBank Accession Nos. 3164125 and 3164126, respectively). The term as used herein encompasses a polynucleotide including a native sequence depicted in FIG. 1, as well as modifications and fragments thereof.

Thus, the term encompasses alterations to the polynucleotide sequence, so long as the alteration results in a molecule displaying CYP83B1 activity, e.g., the ability to metabolize indole-3-acetaldoxime, as described herein. The activity displayed by such mutant molecules need not be at the same level as the native molecule. CYP83B1 activity can be assessed using the methods described herein. Such modifications typically include deletions, additions and substitutions, to the native CYP83B1 sequence. These modifications may be deliberate, as through site-directed mutagenesis, or may be accidental, such as through mutations of plants which express the polypeptide or errors due to PCR amplification. The term encompasses expressed allelic variants of the wild-type sequence which may occur by normal genetic variation or are produced by genetic engineering methods and which result in CYP83B1 activity.

The term "auxin phenotype" as used herein refers to any microscopic or macroscopic change in structure or morphology of a plant, such as a transgenic plant, as well as biochemical differences, which are characteristic of a plant which overproduces or underproduces auxin, compared to a progenitor, wild-type plant cultivated under the same conditions. Generally, such morphological differences include loss or increase of apical dominance, reduced or increased hypocotyl length, reduced or increased number of inflorescences, reduced or increased height, a bushy appearance due to extensive branching and reduced seed set, epinastic cotyledons, exfoliation of the hypocotyl, adventitious root formation from the hypocotyl, enhanced secondary root and root hair formation and, eventually, callus formation and increasing disintegration of the seedling. Additional phenotypic morphological attributes of the auxin phenotype are summarized in Table 1 of the Examples.

In CYP83B1 knock-out plants, the indole-3-acetaldoxime in excess is channeled into IAA biosynthesis leading to elevated IAA levels and thus increased apical dominance and reduced indole glucosinolate levels. Conversely, overexpression of CYP83B1 leads to a reduced IAA phenotype and loss of apical dominance and elevated indole glucosinolate levels, indicating that increased indole-3-acetaldoxime N-oxidation results in a net loss of IAA.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, mutants and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced (see further below).

A "CYP83B1" polypeptide is a polypeptide as defined above, which is derived from the CYP83B1 polypeptide and that retains CYP83B1 enzymatic activity. As explained above, this enzyme is a cytochrome P450 and regulates auxin production in *Arabidopsis* by controlling the flux of indole-3-acetaidoxime into IAA and indole glucosinolate biosynthesis. CYP83B1 also catalyzes the first committed step in indole glucosinolate biosynthesis by metabolizing indole-3-acetaldoxime to its S-alkylthio-hydroximate (see, FIG. 7). The CYP83B1 amino acid sequence is shown in FIG. 2 (GenBank Accession No. 3164126). The term encompasses mutants and fragments of the native sequence so long as the protein functions for its intended purpose.

The term "CYP83B1 analog" refers to derivatives of CYP83B1, or fragments of such derivatives, that retain desired function, e.g., as measured in assays as described further below. In general, the term "analog" refers to compounds having a native polypeptide sequence and structure with one or more amino acid additions, substitutions (generally conservative in nature) and/or deletions, relative to the native molecule, so long as the modifications do not destroy desired activity. Preferably, the analog has at least the same activity as the native molecule. Methods for making polypeptide analogs are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. It is to be understood that the terms include the various sequence polymorphisms that exist, wherein amino acid substitutions in the protein sequence do not affect the essential functions of the protein.

By "purified" and "isolated" is meant, when referring to a polypeptide or polynucleotide, that the molecule is separate and discrete from the whole organism with which the molecule is found in nature; or devoid, in whole or part, of sequences normally associated with it in nature; or a sequence, as it exists in nature, but having heterologous sequences (as defined below) in association therewith. It is to be understood that the term "isolated" with reference to a polynucleotide intends that the polynucleotide is separate and discrete from the chromosome from which the polynucleotide may derive. The term "purified" as used herein preferably means at least 75% by weight, more preferably at least 85% by weight, more preferably still at least 95% by weight, and most preferably at least 98% by weight, of biological macromolecules of the same type are present. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "fragment" is intended a polypeptide or polynucleotide consisting of only a part of the intact sequence and structure of the reference polypeptide or polynucleotide, respectively. The fragment can include a 3' or C-terminal deletion or a 5' or N-terminal deletion, or even an internal deletion, of the native molecule. A polynucleotide fragment of a CYP83B1 sequence will generally include at least about 15 contiguous bases of the molecule in question, more preferably 18–25 contiguous bases, even more preferably 30–50 or more contiguous bases of the CYP83B1 molecule, or any integer between 15 bases and the full-length sequence of the molecule. Fragments which provide at least one CYP83B1 phenotype as defined above are useful in the production of transgenic plants. Fragments are also useful as oligonucleotide probes, to find additional CYP83B1 sequences, e.g., in different plant species.

Similarly, a polypeptide fragment of a CYP83B1 molecule will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length CYP83B1 molecule, or any integer between 10 amino acids and the full-length sequence of the molecule. Such fragments are useful for the production of antibodies and the like.

By "transgenic plant" is meant a plant into which one or more exogenous polynucleotides have been introduced. Examples of means by which this can be accomplished are described below, and include *Agrobacterium*-mediated transformation, biolistic methods, electroporation, and the like. In the context of the present invention, the transgenic plant contains a CYP83B1 polynucleotide which is either over- or underexpressed and which confers at least one auxin phenotypic trait to the plant, as explained above. The transgenic plant therefore exhibits altered structure, morphology or biochemistry as compared with a progenitor plant which does not contain the transgene, when the transgenic plant and the progenitor plant are cultivated under similar or equivalent growth conditions. A transgenic plant may also over- or underexpress glucosinolates. Such a plant containing the exogenous polynucleotide is referred to here as an $R_1$ generation transgenic plant. Transgenic plants may also arise from sexual cross or by selfing of transgenic plants into which exogenous polynucleotides have been introduced. Such a plant containing the exogenous nucleic acid is also referred to here as an $R_1$ generation transgenic plant. Transgenic plants which arise from a sexual cross with another parent line or by selfing are "descendants or the progeny" of a $R_1$ plant and are generally called $F_n$ plants or $S_n$ plants, respectively, n meaning the number of generations.

General Overview

The inventors herein have discovered that CYP83B1, a cytochrome P450, regulates auxin production from tryptophan in *Arabidopsis*. Plants which overexpress or underexpress this enzyme, therefore, have auxin phenotypes, as described above. Thus, plant growth, nutritional values and plant pathogens can be affected by modulating levels of expression of this enzyme.

The molecules of the present invention are therefore useful in the production of transgenic plants which display at least one auxin phenotype, so that the resulting plants have altered structure or morphology. The present invention particularly provides for altered structure or morphology such as reduced cell length, extended flowering periods, increased size of leaves or fruit, increased branching, and increased seed production relative wild-type plants. The CYP83B1 polypeptides can be expressed to engineer a plant with desirable properties. The engineering is accomplished by transforming plants with nucleic acid constructs described herein which may also comprise promoters and secretion signal peptides. The transformed plants or their progenies are screened for plants that express the desired polypeptide.

Engineered plants exhibiting the desired altered structure or morphology can be used in plant breeding or directly in agricultural production or industrial applications. Plants having the altered phenotypes can be crossed with other altered plants engineered with alterations in other growth modulation enzymes, proteins or polypeptides to produce lines with even further enhanced altered structural morphology characteristics compared to the parents or progenitor plants.

The present invention also pertains to methods of producing glucosinolates and indole-3-acetic acid. Glucosinolates are hydrophilic, non-volatile thioglycosides found within several orders of dicotyledoneous angiosperms (Cronquist, The Evolution and Classification of Flowering Plants, New York Botanical Garden, Bronx, 1988). The greatest economic significance of glucosinolates is their presence in all members of the *Brassicaceae* (order of *Capparales*) that are a source of condiments, relishes, salad crops and vegetables as well as fodders and forage crops. Additionally, these compounds are pharmaceutically significant and may find use as anti-cancer agents. More recently, rape (especially *Brassica napus* and *Brassica campestris*) has emerged as a major oil seed of commerce.

About 100 different glucosinolates are known which possess the same general chemical structure but differ in the nature of the side chain. Generally, glucosinolates are grouped into three different classes: aliphatic, aromatic and indole, depending on whether they are derived from aliphatic amino acids, aromatic amino acids, or tryptophan. The amino acids can be converted into glucosinolates either directly or after the side chains on the amino acids have been modified, for example, by chain-elongation. Initially, the amino acids or chain-elongated amino acids are converted to the labile aldoximes by cytochrome P450s, the aldoximes are hydroxylated by another cytochrome P450 of the CYP83 family and eventually metabolized to form a glucosinolate.

The glucosinolates are derived from only seven protein amino acids, namely alanine, valine, leucine, isoleucine, tyrosine, tryptophan, and phenylalanine, chain-elongated forms thereof, as well as homophenylalanine and several chain-elongated homologues of methionine. In vivo biosynthetic studies have shown that N-hydroxyamino acids, nitro compounds, aldoximes, thiohydroximates, and desulfoglucosinolates are precursors of glucosinolates.

The first step in the biosynthesis of glucosinolate and indole glucosinolates is catalyzed by cyctochromes P450 of the CYP79 subfamily. CYP79 catalyzes the conversion of amino acids to their corresponding aldoximes via N-hydroxyamino intermediates. The aldoximes are then acted on by another subfamily of cytochromes P450, namely CYP83A1 and CYP83B1 convert aldoximes to glucosinolates and indole glucosinolates respectively. The cytochromes are thought to act by adding a hydroxyl group at the nitrogen atom of the oxime function generates a highly reactive aci-nitro compound. The α-carbon atom of the aci-nitro compound is a target for a nucleophilic attack from a sulfhydryl group, resulting in the formation of the corresponding S-alkylthiohydroximate or indole-3-S-alkylthiohydroximate. The S-alkylthiohydroximate can be cleaved presumably by a C-S lyase to generate thiohydroximates. It is well established that thiohydroximates are glucosylated by a soluble UDPG:thiohydroximate glucosyltransferase to form desulfoglucosinolates that are subsequently sulfated. Thus, for the biosynthesis of indole glucosinolates, tryptophan is catalyzed by CYP79B2 or CYP79B3 to indole-3-acetaldoxime. CYP83B1 catalyzes the conversion of indole-3-acetaldoxime to 1-aci-nitro-2-indolyl-ethane which converts to S-cysteinyl-thiohydroximate which in turn converts to indole glucosinolates.

Isolation of Nucleic Acid Sequences from Plants

The isolation of CYP83B1 polynucleotides may be accomplished by a number of techniques. For instance, oligonucleotide probes based on the sequences disclosed herein can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species. Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR.RTM and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying CYP83B1-specific genes from plant tissues are generated from comparisons of the sequences provided herein. For a general overview of PCR see Innis et al. eds, *PCR Protocols: A Guide to Methods and Applications*, Academic Press, San Diego (1990). Appropriate primers for this invention include, for instance, primers derived from the CYP83B1 polynucleotide sequence depicted in FIG. 1 herein. Suitable amplifications conditions may be readily determined by one of skill in the art in view of the teachings herein, for example, including reaction components and amplification conditions as follows: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase; 96° C. for 3 min., 30 cycles of 96° C. for 45 seconds, 50° C. for 60 seconds, 72° C. for 60 seconds, followed by 72° C. for 5 min.

Polynucleotides may also be synthesized by well-known techniques as described in the technical literature. See, e.g., Carruthers, et al. (1982) Cold Spring Harbor Symp. Quant. Biol. 47:411–418, and Adams, et al. (1983) J. Am. Chem. Soc. 105:661. Double stranded DNA fragments may then be obtained either by synthesizing the complementary strand and annealing the strands together under appropriate conditions, or by adding the complementary strand using DNA polymerase with an appropriate primer sequence.

The polynucleotides of the present invention may also be used to isolate or create other mutant cell gene alleles. Mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Control Elements

Regulatory regions can be isolated from the CYP83B1 gene and used in recombinant constructs for modulating the expression of the gene or a heterologous gene in vitro and/or in vivo. This region may be used in its entirety or fragments of the region may be isolated which provide the ability to direct expression of a coding sequence linked thereto.

Thus, promoters can be identified by analyzing the 5' sequences of a genomic clone including the CYP83B1 gene and sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. (See, J. Messing et al., in Genetic Engineering in Plants, pp. 221–227 (Kosage, Meredith and Hollaender, eds. (1983)). Methods for identifying and characterizing promoter regions in plant genomic DNA are described, for example, in Jordano et al. (1989) Plant Cell 1:855–866; Bustos et al (1989) Plant Cell 1:839–854; Green et al. (1988) EMBO J. 7:4035–4044; Meier et al. (1991) Plant Cell 3:309–316; and Zhang et al (1996) Plant Physiology 110:1069–1079).

Additionally, the promoter region may include nucleotide substitutions, insertions or deletions that do not substantially affect the binding of relevant DNA binding proteins and hence the promoter function. It may, at times, be desirable to decrease the binding of relevant DNA binding proteins to "silence" or "down-regulate" a promoter, or conversely to increase the binding of relevant DNA binding proteins to "enhance" or "up-regulate" a promoter. In such instances, the nucleotide sequence of the promoter region may be modified by, e.g., inserting additional nucleotides, changing the identity of relevant nucleotides, including use of chemically-modified bases, or by deleting one or more nucleotides.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

Polynucleotides comprising untranslated (UTR) sequences and intron/exon junctions may also be identified. UTR sequences include introns and 5' or 3' untranslated regions (5' UTRs or 3' UTRs). These portions of the gene, especially UTRs, can have regulatory functions related to, for example, translation rate and mRNA stability. Thus, these portions of the gene can be isolated for use as elements of gene constructs for expression of polynucleotides encoding desired polypeptides.

Introns of genomic DNA segments may also have regulatory functions. Sometimes promoter elements, especially transcription enhancer or suppressor elements, are found within introns. Also, elements related to stability of heteronuclear RNA and efficiency of transport to the cytoplasm for translation can be found in intron elements. Thus, these segments can also find use as elements of expression vectors intended for use to transform plants.

The introns, UTR sequences and intron/exon junctions can vary from the native sequence. Such changes from those sequences preferably will not affect the regulatory activity of the UTRs or intron or intron/exon junction sequences on expression, transcription, or translation. However, in some instances, down-regulation of such activity may be desired to modulate traits or phenotypic or in vitro activity.

Use of Nucleic Acids of the Invention to Inhibit Gene Expression

The isolated sequences prepared as described herein, can be used to prepare expression cassettes useful in a number of techniques. For example, expression cassettes of the invention can be used to suppress (underexpress) endogenous CYP83B1 gene expression. Inhibiting expression can be useful, for instance, in producing an auxin phenotype, as described above. Further, the inhibitory polynucleotides of the present invention can also be used in combination with overexpressing constructs described below, for example, using suitable tissue-specific promoters linked to polynucleotides described herein. In this way, the polynucleotides can be used to modulate auxin phenotypes in selected tissue and, at the same time, modulate auxin phenotypes in different tissue(s).

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, antisense RNA may inhibit gene expression by preventing the accumulation of mRNA which encodes the enzyme of interest, see, e.g., Sheehy et al (1988) *Proc. Nat. Acad. Sci. USA* 85:8805–8809, and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. It is to be understood that any integer between the above-recited ranges is intended to be captured herein.

Catalytic RNA molecules or ribozymes can also be used to inhibit expression of CYP83B1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al (1988) *Nature* 334:585–591.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al (1990) *The Plant Cell* 2:279–289 and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 50%–65%, but a higher identity might exert a more effective repression of expression of the endogenous sequences. Substantially greater identity of more than about 80% is preferred, though about 95% to absolute identity would be most preferred. It is to be understood that any integer between the above-recited ranges is intended to be captured herein. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Use of Nucleic Acids of the Invention to Enhance Gene Expression

The present invention may also be used to overexpress CYP83B1. For example, by operably linking the CYP83B1 coding sequence to a promoter which allows for overexpression of the gene. (See the discussion regarding promoters below.) The exogenous CYP83B1 polynucleotides do not have to code for exact copies of the endogenous CYP83B1 proteins. Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al (1991) *Meth. Enzymol.* 194: 302–318). For example, the chains can vary from the naturally occurring sequence at the primary structure level by amino acid substitutions, additions, deletions, and the like. These modifications can be used in a number of combinations to produce the final modified protein chain.

It will be apparent that the polynucleotides described herein can be used in a variety of combinations. For example, the polynucleotides can be used to produce different phenotypes in the same organism, for instance by using tissue-specific promoters to overexpress a CYP83B1 polynucleotide in certain tissues (e.g., leaf tissue) while at the same time using tissue-specific promoters to inhibit expression of in other tissues. In addition, fusion proteins of the polynucleotides described herein with other known polynucleotides (e.g., polynucleotides encoding products involved in the brassinosteroid pathway) can be constructed and employed to obtain desired phenotypes.

Any of the polynucleotides described herein can also be used in standard diagnostic assays, for example, in assays for mRNA levels (see, Sambrook et al, supra); as hybridization probes, e.g., in combination with appropriate means, such as a label, for detecting hybridization (see, Sambrook et al., supra); as primers, e.g., for PCR (see, Sambrook et al., supra); attached to solid phase supports and the like.

Preparation of Recombinant Vectors

To use isolated sequences in the above techniques, recombinant DNA vectors suitable for transformation of plant cells are prepared. Techniques for transforming a wide variety of higher plant species are well known and described further below as well as in the technical and scientific literature. See, for example, Weising et al (1988) *Ann. Rev. Genet.* 22:421–477. A DNA sequence coding for the desired polypeptide, for example a cDNA sequence encoding the full-length CYP83B1 protein, will preferably be combined with transcriptional and translational initiation regulatory sequences which will direct the transcription of the sequence from the gene in the intended tissues of the transgenic plant.

Such regulatory elements include but are not limited to the promoters derived from the genome of plant cells (e.g., heat shock promoters such as soybean hsp17.5-E or hsp17.3-B (Gurley et al. (1986) *Mol. Cell. Biol.* 6:559–565); the promoter for the small subunit of RUBISCO (Coruzzi et al. (1984) *EMBO J.* 3:1671–1680; Broglie et al (1984) *Science* 224:838–843); the promoter for the chlorophyll a/b binding protein) or from plant viruses viral promoters such as the 35S RNA and 19S RNA promoters of CaMV (Brisson et al. (1984) *Nature* 310:511–514), or the coat protein promoter of TMV (Takamatsu et al. (1987) *EMBO J.* 6:307–311), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, heat shock promoters (e.g., as described above) and the promoters of the yeast alpha-mating factors.

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the T-DNA mannopine synthetase promoter (e.g., the 1'- or 2'-promoter derived from T-DNA of *Agrobacterium tumafaciens*), and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers such as tissue- or developmental-specific promoter, such as, but not limited to the CHS promoter, the PATATIN promoter, etc. The tissue specific E8 promoter from tomato is particularly useful for directing gene expression so that a desired gene product is located in fruits.

Other suitable promoters include those from genes encoding embryonic storage proteins. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA. In addition, the promoter itself can be derived from the CYP83B1 gene, as described above.

The vector comprising the sequences (e.g., promoters or coding regions) from CYP83B1 will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transgenic Plants

DNA constructs may be introduced into the genome of the desired plant host by a variety of conventional techniques. For reviews of such techniques see, for example, Weissbach & Weissbach *Methods for Plant Molecular Biology* (1988, Academic Press, N.Y.) Section VIII, pp. 421–463; and Grierson & Corey, *Plant Molecular Biology* (1988, 2d Ed.), Blackie, London, Ch. 7–9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70–73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496–498, and Fraley et al (1983) *Proc. Nat'l. Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711–8721) or the co-cultivation procedure (Horsch et al (1985) *Science* 227: 1229–1231). Generally, the *Agrobacterium* transformation system is used to engineer dicotyledonous plants (Bevan et al (1982) *Ann. Rev. Genet* 16:357–384; Rogers et al (1986) *Methods Enzymol.* 118:627–641). The *Agrobacterium* transformation system may also be used to transform, as well as transfer, DNA to monocotyledonous plants and plant cells. (see Hernalsteen et al (1984) *EMBO J* 3:3039–3041; Hooykass-Van Slogteren et al (1984) *Nature* 311:763–764; Grimsley et al (1987) *Nature* 325:1677–179; Boulton et al (1989) *Plant Mol. Biol.* 12:31–40; and Gould et al (1991) *Plant Physiol.* 95:426–434).

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717–2722, Potrykus et al. (1985) *Molec. Gen. Genet.* 199:169–177; Fromm et al. (1985) *Proc. Nat. Acad. Sci. USA* 82:5824–5828; and Shimamoto (1989) *Nature* 338:274–276) and electroporation of plant tissues (D'Halluin et al. (1992) *Plant Cell* 4:1495–1505). Additional methods for plant cell transformation include microinjection, silicon carbide mediated DNA uptake (Kaeppler et al. (1990) *Plant Cell Reporter* 9:415–418), and microprojectile bombardment (see Klein et al. (1988) *Proc. Nat. Acad. Sci. USA* 85:4305–4309; and Gordon-Kamm et al. (1990) *Plant Cell* 2:603–618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in vans, et al., "Protoplasts Isolation and Culture" in *Handbook of Plant Cell Culture*, pp. 124–176, Macmillian Publishing Company, New York, 1983; and Binding, *Regeneration of Plants, Plant Protoplasts*, pp. 21–73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467–486.

The nucleic acids of the invention can be used to confer desired traits on essentially any plant. A wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the invention has use over a broad range of plants, including, but not limited to, species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods of this invention can be observed by, for example, northern blots of the RNA (e.g., mRNA) isolated from the tissues of interest. Typically, if the amount of mRNA has increased, it can be assumed that the endogenous CYP83B1 gene is being expressed at a greater rate than before. Other methods of measuring CYP83B1 activity can be used. For example, cell length can be measured at specific times. Because CYP83B1 affects the auxin biosynthetic pathway, an assay that measures the amount of auxin can also be used, as well as assays that measure the direct step where CYP83B1 is involved. Such assays are known in the art. Different types of enzymatic assays can be used, depending on the substrate used and the method of detecting the increase or decrease of a reaction product or by-product. In addition, the levels of CYP83B1 protein expressed can be measured immunochemically, i.e., ELISA, RIA, EIA and other antibody based assays well known to those of skill in the art, by electrophoretic detection assays (either with staining or western blotting), and auxin detection assays.

The transgene may be selectively expressed in some tissues of the plant or at some developmental stages, or the transgene may be expressed in substantially all plant tissues, substantially along its entire life cycle. However, any combinatorial expression mode is also applicable.

The present invention also encompasses seeds of the transgenic plants described above wherein the seed has the transgene or gene construct. The present invention further encompasses the progeny, clones, cell lines or cells of the transgenic plants described above wherein said progeny, clone, cell line or cell has the transgene or gene construct.

Polypeptides

The present invention also includes CYP83B1 polypeptides, including such polypeptides as a fusion, or chimeric protein product (comprising the protein, fragment, analogue, mutant or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

As noted above, the auxin phenotype due to over or underexpression of CYP83B1 includes any macroscopic, microscopic or biochemical changes which are characteristic of over or underexpression of auxin. Thus, the phenotype (e.g., activities) can include any activity that is exhibited by the native CYP83B1 polypeptide including, for example, in vitro, in vivo, biological, enzymatic, immunological, substrate binding activities, etc. Non-limiting examples of such activities include:

(a) activities displayed by other heme-thiolate enzymes;

(b) characteristic Soret absorption peak at 450 nm when the substrate-bound reduced form is exposed to the lights (see, e.g., Jefcoate C. R. (1978) *Methods Enzymol* 27:258–279);

(c) oxidation, dealkylation, deaminoation, dehalogenation, and sulfoxide formation that are involved in a variety of biological events in plants and animals (e.g., catabolism, anabolism, and xenobiotic activities);

(d) activity on indole-e-acetaldoxime;

(e) auxin phenotypic activities such as modulation of cell length, periods of flowering, branching, seed production and leaf size;
(f) regulation of auxin and glucosinolate; and
(g) induce resistance to plant pathogens (see, e.g., U.S. Pat. No. 5,952,545).

A CYP83B1 analog, whether a derivative, fragment or fusion of native CYP83B1 polypeptides, is capable of at least one CYP83B1 activity. Preferably, the analogs exhibit at least 60% of the activity of the native protein, more preferably at least 70% and even more preferably at least 80%, 85%, 90% or 95% of at least one activity of the native protein.

Further, such analogs exhibit some sequence identity to the native CYP83B1 polypeptide sequence. Preferably, the variants will exhibit at least 35%, more preferably at least 59%, even more preferably 75% or 80% sequence identity, even more preferably 85% sequence identity, even more preferably, at least 90% sequence identity; more preferably at least 95%, 96%, 97%, 98% or 99% sequence identity.

CYP83B1 analogs can include derivatives with increased or decreased activities as compared to the native CYP83B1 polypeptides. Such derivatives can include changes within the domains, motifs and/or consensus regions of the native CYP83B1 polypeptide.

One class of analogs is those polypeptide sequences that differ from the native CYP83B1 polypeptide by changes, insertions, deletions, or substitution; at positions flanking the domain and/or conserved residues. For example, an analog can comprise (1) the domains of a CYP83B1 polypeptide and/or (2) at conserved or nonconserved residues. For example, an analog can comprise residues conserved between the CYP83B1 polypeptide and other cytochrome P450 proteins with other regions of the molecule changed.

Another class of analogs includes those that comprise a CYP83B1 polypeptide sequence that differs from the native sequence in the domain of interest or conserved residues by a conservative substitution.

Yet another class of analogs includes those that lack one of the in vitro activities or structural features of the native CYP83B1 polypeptides, for example, dominant negative mutants or analogs that comprise a heme-binding domain but other inactivated domains.

CYP83B1 polypeptide fragments can comprise sequences from the native or analog sequences, for example fragments comprising one or more of the following P450 domains or regions: A, B, C, D, anchor binding, and proline rich. Such domains and regions are known.

Fusion polypeptides comprising CYP83B1 polypeptides (e.g., native, analogs, or fragments thereof) can also be constructed. Non-limiting examples of other polypeptides that can be used in fusion proteins include chimeras of CYP83B1 polypeptides and fragments thereof; and other known P450 polypeptides or fragments thereof.

In addition, CYP83B1 polypeptides, derivatives (including fragments and chimeric proteins), mutants and analogues can be chemically synthesized. See, e.g., Clark-Lewis et al. (1991) *Biochem.* 30:3128–3135 and Merrifield (1963) *J. Amer. Chem. Soc.* 85:2149–2156. For example, CYP83B1, derivatives, mutants and analogues can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). CYP83B1, derivatives and analogues that are proteins can also be synthesized by use of a peptide synthesizer.

The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

Further, the polynucleotides and polypeptides described herein can be used to generate antibodies that specifically recognize and bind to the protein products of the CYP83B1 polynucleotides. (See, Harlow and Lane, eds. (1988) "Antibodies: A Laboratory Manual"). The polypeptides and antibodies thereto can also be used in standard diagnostic assays, for example, radioimmunoassays, ELISA (enzyme linked immunoradiometric assays), "sandwich" immunoassays, immunoradiometric assays, in situ immunoassay, western blot analysis, immunoprecipitation assays, immunofluorescent assays and PAGE-SDS.

Applications

The present invention finds use in various applications, for example, including but not limited to those listed above. In particular, the present invention contemplates production of transgenic plants that over or underexpress CYP83B, thereby producing any of the various auxin phenotypes specified above. Thus, the CYP83B1 polynucleotides may be placed in recombinant vectors which may be inserted into host cells to express the CYP83B1 protein, under the control of promoters that either enhance or decrease CYP83B1 expression.

The nucleic acid molecules may be used to design plant CYP83B1 antisense molecules, useful, for example, in plant CYP83B1 gene regulation or as antisense primers in amplification reactions of plant gene nucleic acid sequences. With respect to plant gene regulation, such techniques can be used to regulate, for example, plant growth, development or gene expression. Further, such sequences may be used as part of ribozyme and/or triple helix sequences, also useful for gene regulation.

Thus, the molecules of the present invention can be used to provide plants with increased seed and/or fruit production, extended flowering periods and increased branching, by altering the auxin composition of a plant. A still further utility of the molecules of the present invention is to provide a tool for studying the biosynthesis of auxins, both in vitro and in vivo.

The *Arabidopsis* CYP83B1 protein can be used in any biochemical applications (experimental or industrial), for example, but not limited to, regulation of auxin and glucosinolate synthesis, modification of elongating plant structures, and experimental or industrial biochemical applications known to those skilled in the art.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Plants. Plants were grown at a photosynthetic flux of 100–120 $\mu$mol photons m$^{-2}$s$^{-1}$ and 70% humidity, 22° C. for a 12 h photo period. Morphometric analyses are shown with their S.E.M.

rnt1-1 was backcrossed once to wild type Wassilewskija-2 *Arabidopsis*. Rnt progeny from the backcross were used for all further analysis. For molecular complementation of rnt1-1, a 5574 hp DNA fragment containing 2276 hp upstream of the start codon and 1703 hp downstream of the stop codon was inserted into the binary vector pPZP221 (Hajdukiewicz et al. (1994) *Plant Mol Biol* 25:989–994) harboring gentamycin resistance and transformed into rnt1-1/RNT1 plants by the floral dip method. Primary transformants were selected on MS plates supplemented with 2% sucrose, 0.9% Bacto agar, 50 μg/ml kanamycin and 200 μg/ml gentamycin. Lines homozygous for the T-DNA insertion in CYP83B1 and harboring the introduced 5.5 kb DNA fragment were identified by co-segregation analysis on selective MS agar plates. Overexpression constructs comprising the CYP83B1 cDNA under control of a cauliflower mosaic virus 35S promoter and polyadenylation site were made in pPZP221.

Double mutants of nit1-1 and rnt1-1 were made by crossing rnt1-1/RNT1 (Wassilewskija-2), (pollen donor) into nit1-1 (Columbia Col-0). Double mutants homozygous for nit1-1 were identified according to (Normanly et al. (1997) *Plant Cell* 9:1781–1790) and verified by sequence analysis. To account for possible ecotypic differences, rnt1-1 was crossed into wild type Columbia Col-0. No ecotypic differences of the rnt1-I phenotype were observed in the Columbia ecotype compared to Wassilewskija-2.

Analysis of recombinant CYP83B1 enzyme. Microsomes from yeast WAT1 I cells expressing the CYP83B1 cDNA using the pYeDP60 vector were isolated essentially according to (Pompon et al. (1996) *Methods Enzymol*. 272:51–64). Indole-3-acetaldoxime was synthesized from indole-3-acetaldehyde according to (Rausch et al. (1985) *J. Chromatog.* 318:95–102). The structure of indole-3acetaldoxime was confirmed by $^1$H NMR, ES-MS and GC-MS. [5-$^3$H]indole-3-acetaldoxime was synthesized from [5-$^3$H]L-tryptophan according to (Hofmann et al. (1980) *J Label. Comp. Radiopharm.* 18:1491–1495). Binding spectra were recorded using 0.44 μM CYP83B1 on a Lambda19 spectrophotometer (Perkin Elmer). To determine the spectral dissociation constant Ks of tryptamine, we used 9 concentrations ranging from 2.2 μM to 160 μM. To determine the Ks of indole-3-acetaldoxime, we used 11 concentrations ranging from 0.2 μM to 7 μM.

For analysis of CYP83B1 catalysis reaction mixtures of 25 μl containing 8.8 nM CYP83B1 (7), 6% glycerol, 50 mM Tris-HCl pH 7.6, 70 μM [5-$^3$H]indole-3-acetaldoxime; specific activity 350 mCi/mmol, 0.1 mM NADPH, 2 mM glucose-6-phosphate, 0.075 units glucose-6-phosphate dehydrogenase, and 10 mM cysteine or other nucleophiles as indicated were incubated for 15 min at 28° C. After incubation, reaction mixtures were stopped by adding SDS to 0.4% and were analyzed by thin layer chromatography (TLC). TLC plates were developed in chloroform/methanol/water (85:14:1) and radioactive bands visualized by autoradiography.

To determine $K_m$ and $V_{max}$ reaction mixtures containing 2.2 nM CYP83B1 and 0.2 to 60 μM [5-$^3$H]indole-3-acetaldoxime and 50 mM L-cysteine were incubated for 1 min at 28° C. Reactions were stopped and extracted with ethylacetate. Aliquots of the substrate-containing ethylacetate phase and product-containing water phase were subjected to liquid scintillation counting.

For structural analysis, reaction mixtures of 100 μl containing 0.5 μM CYP83B1, I mM indole-3-acetaldoxime, 10 mM β-mercaptoethanol, 50 mM MOPS pH 7.6, 0.1 mM NADPH, 2 mM glucose-6-phosphate, 0.2 units glucose-6-phosphate dehydrogenase, and 6% glycerol were incubated at 28° C. After incubation, reaction mixtures were extracted with ethylacetate and dried. For ES-MS samples were dissolved in acetonitrile. For GC-EIMS and GC-CIMS analysis the samples were then derivatized for 20 min at 90° C. with a 30 μl 1:1 mixture of bis-trimethylsilyltrifluoroacetamide:pyridine containing 1% trimethylchlorosilane prior to analysis. For GC-MS analysis we used a VA-5MS column (10 m×0.25 mm×0.25 gm film thickness). The oven temperature program used was as follows: 100° C. for 2 min, 100–250° C. at 10° C. min$^{-1}$, 250° C. for 10 min.

Example 1

CYP83B1 is Essential for Normal Seedling Development

CYP83B1 was shown to be essential for normal seedling development as follows. A null mutation of CYP83B1 was identified by a systematic reverse genetics approach for T-DNA mediated gene disruptions of cytochromes P450 in *Arabidopsis* (Winkler et al. (1998) *Plant Physiol.* 118: 743–750). This mutation was called rnt1–1 in view of its runt phenotype. The T-DNA was inserted in the first exon of the CYP83B1 gene between position 316 and 325 relative to the start codon. Eight basepairs of CYP83B1 were deleted at the insertion site. The entire sequence of chromosome 4 obtained recently (Mayer et al. (1999) *Nature* 402:769–777) revealed that amongst the approximately 50 P450 genes of chromosome 4, CYP83B1 maps most closely to the prha marker which is within 1.3 cM of sur2 (Delarue et al. (1998) *Plant J*. 14:603–611). This strongly suggested that rnt1-l is an allele of sur2, a mutant know to accumulate elevated levels of free IAA (Delarue et al. (1998) *Plant J*. 14:603–611). Recently, sur2 was indeed demonstrated to be a CYP83B1 mutant (C. Bellini, personal communication). As described for sur2 seedlings, rnt1-1 seedlings were characterized by having increased hypocotyl length, epinastic cotyledons, exfoliation of the hypocotyl, adventitious root formation from the hypocotyl, enhanced secondary root and root hair formation and eventually callus formation and increasing disintegration of the seedling (Table 1). The majority of rnt1-1 seedlings never developed more than a few leaves before the organization of the tissue was lost. In soil, a minority of seedlings were able to overcome the initial defects and develop into plants with strong apical dominance, characterized by reduced height, an increased number of epinastic rosette leaves, and a single inflorescence (Table 1), a phenotype historically associated with auxin overproduction (Davies P. J. (1995) In *Plant Hormones* Kluwer Academic Publishers, Dordrecht, The Netherlands, pp 1–12). Rnt1-1 differed from sur2 in two major aspects. Exfoliation was observed at the root hypocotyl junction in rnt1-1, whereas in sur2 exfoliation starts in the middle of the hypocotyl. Therefore, with respect to exfoliation, rnt1-1 was more similar to sur1 (for a comparison of sur1 and sur2 see Delarue et al. (1998) *Plant J*. 14:603–611). Rnt1-l plants grown in soil did not display a wild-type appearance (Table 1), whereas sur2 grown in soil did (Delarue et al. (1998) *Plant J*. 14:603–611). The phenotype of rnt1-1 therefore appears to be stronger than that observed for sur2.

That the increased auxin phenotype is due to knock-out of the CYP83B1 gene is demonstrated by molecular complementation of rnt1-1 with a 5.5 kbp genomic fragment that comprises the CYP83B1 gene. Of 18 independent lines, none displayed the hypocotyl disintegration phenotype at the seedling stage. Overexpression of a CYP83B1 cDNA under control of the constitutive cauliflower mosaic virus 35S promoter generated lines with reduced hypocotyl length and increased number of inflorescences as e.g. the 1.4.7 line. Whereas the wild type has typically three inflorescences and rnt1-1 had one, the molecularly complemented line, 3.25.11, and the 1.4.7 overexpression line have between 3–6 inflorescences. More severe overexpression phenotypes included reduced height, a bushy appearance due to extensive branching and reduced seed set. These bushy plants with decreased height and seed set were phenotypically similar to strong alleles of acxr 1 plants, which are characterized by showing decreased apical dominance due to reduced sensing of auxin (Lincoln et al. (1990) *Plant Cell* 2:1071–1080).

Example 2

Spectral Characterization of Heterologously Expressed CYP83B1 Enzyme

To elucidate the biochemical function of CYP83B1, the enzyme was produced in yeast. Yeast microsomes containing CYP83B1 were screened with auxin-related molecules to identify potential ligands by spectral analysis. Tryptamine was found to cause a typical type IIa binding spectrum (Jefcoate C. R. (1978) *Methods Enzymol* 27:258–279) with a trough at 390 nm and a peak at 427 nm and with a spectral dissociation constant Ks of 24 $\mu$M. The type Ia spectrum indicates access of the amine to the vicinity of the heme active site. In addition to tryptamine, other aromatic primary amines also produced similar spectra changes, but none with the same high amplitude or low dissociation constant.

Indole-3-acetaldoxime caused a weak reverse type I spectrum (Jefcoate C. R. (1978) *Methods Enzymol* 27:258–279) with a trough at 385 nm and a peak at 400 nm (data not shown), indicative of binding to the active site. To quantify the affinity of indole-3-acetaldoxime to CYP83B1 properly, the enzyme was first saturated with 100 $\mu$M tryptamine. Subsequently, tryptamine was displaced from the active site by titration with indole-3-acetaldoxime, causing a gradual appearance of a reverse type IIa spectrum, from which a Ks of 0.2 $\mu$M for indole-3-acetaldoxime was estimated (FIG. 3). Indole-3-acetaldoxime is therefore a high affinity ligand for CYP83B1 and the ability of indole-3-acetaldoxime to displace tryptamine argues that tryptamine is a competitive inhibitor that binds to the active site of CYP83B1.

Example 3

Figure 4:
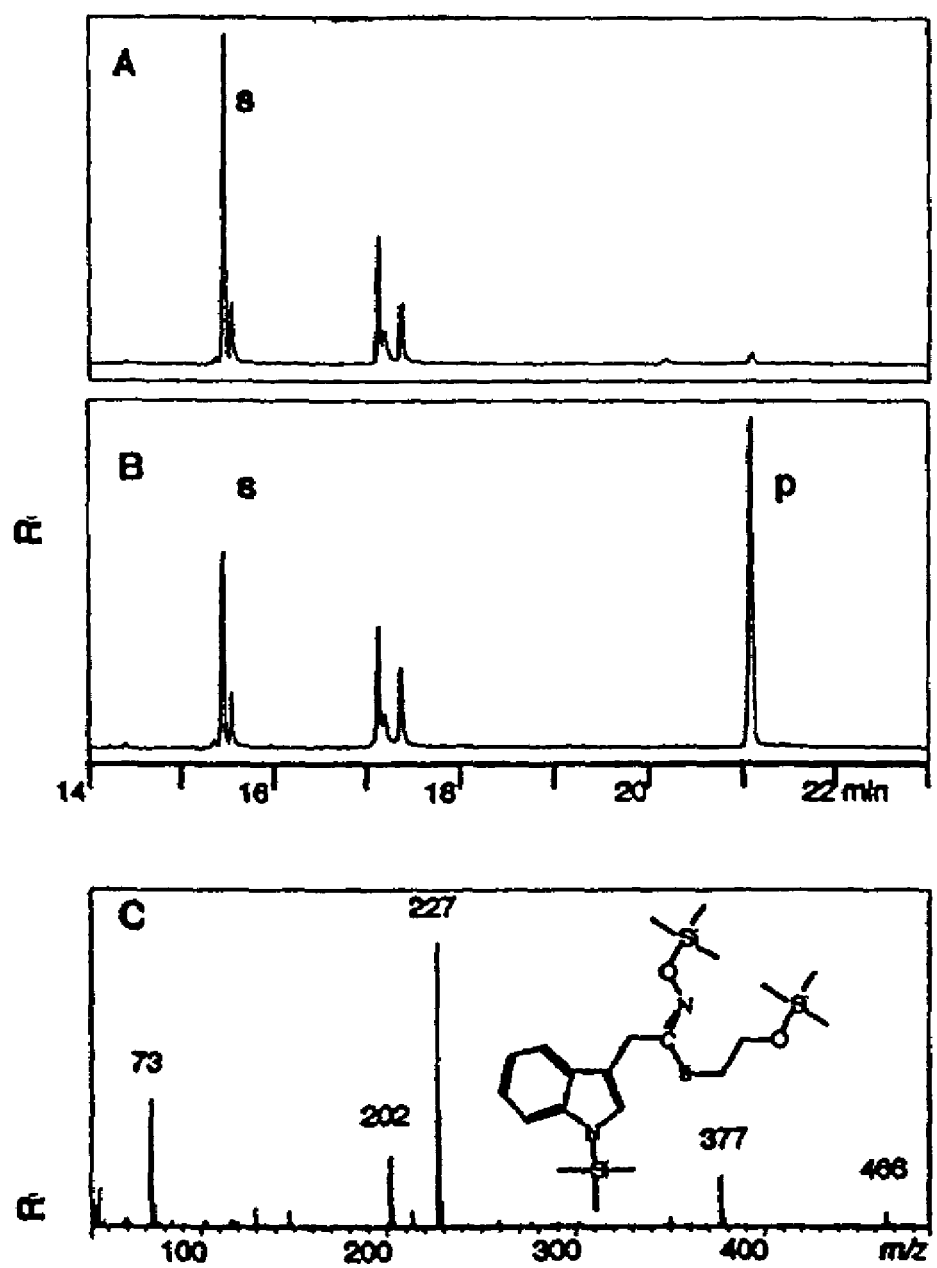
FIG. 4. Analysis of reaction mixtures using GC-EIMS. After incubation for either 0 (A) and 15 min (B) at 28° C., reaction mixtures were subjected to GC-EIMS analysis (C). TMS derivative of indole-3-acetaidoxime (15.467 min) (s), TMS derivative of the b-mercaptoethanol adduct of the reaction mixture (p). The new peak (p) at 21.083 min shows a molecular ion at m/z 466 and a fragmentation pattern consistent with the structure shown in the insert with m/z 377, loss of the oxime O-TMS; m/z 228, further loss of S—C$_2$H$_5$—O—TMS; m/z 202, further loss of nitrile, and m/z 73, TMS. The structure was verified by ES-MS of underivatized ethylacetate extracted reaction mixtures.

CYP83B1 Catalyzes the Oxime Metabolizing Step in Indole Glucosinolate Biosynthesis Isolated yeast microsomes containing CYP83B1 and *Arabidopsis* NADPH cytochrome P450 reductase catalyzed the metabolism of indole-3-acetaldoxime to a single product which was identified by mass spectrometry as a covalent adduct with the major nucleophile present in the reaction mixture (FIG. 4). These S-alkyl-thiohydroximate adducts were observed with a variety of nucleophiles, showing that formation of the adducts was independent of the structure of the nucleophile and was not limiting under the experimental conditions. Nucleophiles tested and the Rf by thin layer chromatography of the adducts formed were: $\beta$-mercaptoethanol (Rf 0.37), L-cysteine (Rf 0.04), ethanethiol (Rf 0.54), 1-thio-$\beta$-D-glucose (Rf 0.02), and reduced glutathione (Rf 0.01). In the absence of added nucleophile the product of the enzymatic reaction inactivated the enzyme. In the presence of cysteine, the Michaelis-Menten constant $K_m$ for indole-3-acetaldoxime was estimated to be 3 $\mu$M and the turnover 53 min$^{-1}$. In accordance with the spectral data, tryptamine was found to be an inhibitor of indole-3-acetaldoxime-oxidation (FIG. 3B).

Figure 5:
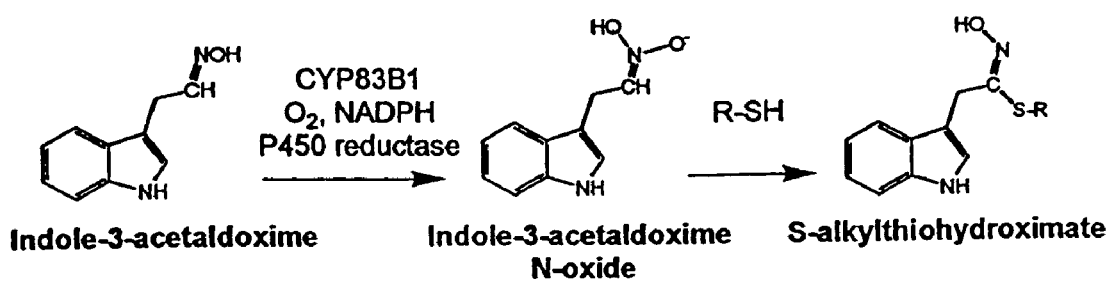
FIG. 5. Proposed reaction scheme of CYP83B1. CYP83B1 catalyzes the first committed step of indole glucosinolate biosynthesis, the N oxidation of indole-3-acetaldoxime to a highly reactive electrophile aci nitro compound that nonenzymatically forms an adduct with a nucleophile (R-SH).

It appears that the S-alkyl-thiohydroximate is formed by oxidation of the nitrogen atom at the oxime function to generate an electrophilic aci-nitro compound, indole-3-acetaldoxime-N-oxide, that forms an adduct with nucleophiles at the $\alpha$-carbon (FIG. 5).

Example 4

Figure 6:
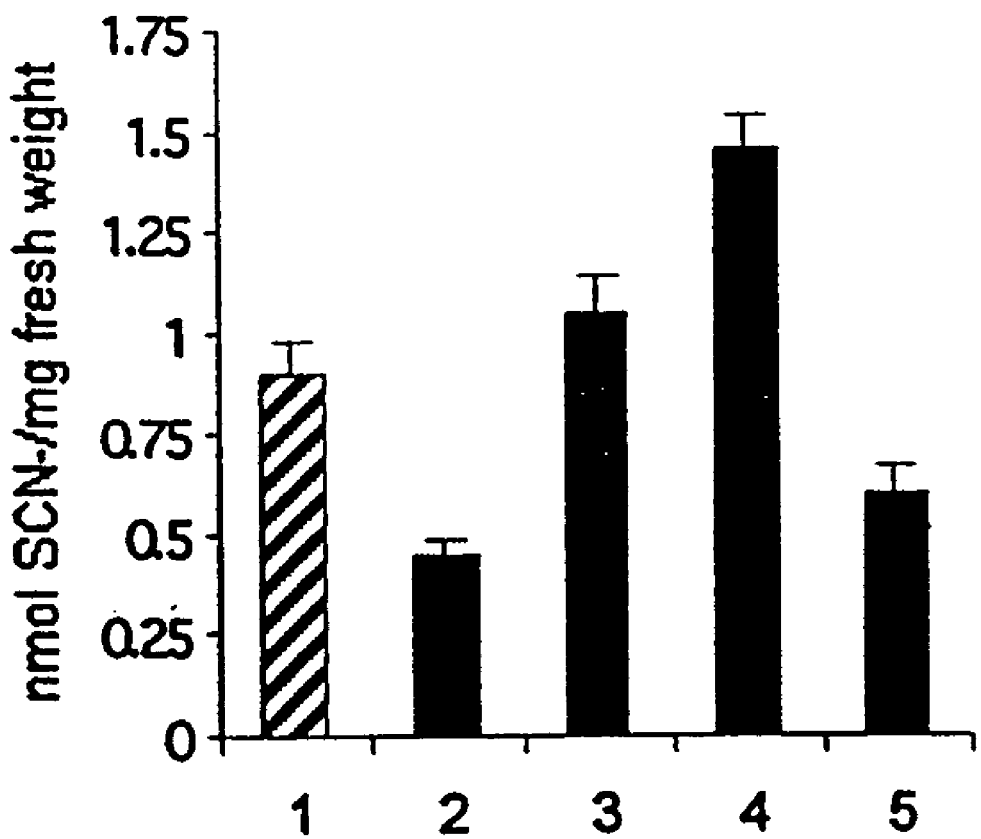
FIG. 6. Indole glucosinolate levels are affected by CYP83B1 expression. Indole glucosinolates in individual two week old seedlings grown on MS agar were quantified calorimetrically as SCN. 1) Wild type, 2) rnt1-1, 3) molecularly complemented line 3.25.11, 4) overexpression line 1.4.7, and 5) wild type grown on 100 μM tryptamine. Data are represented as the mean±S.E, (n=10 seedlings). Except for the molecularly complemented line 3.25.11, mean indole glucosinolate values all differ from wild type seedling values at a 1% confidence value (t-test).

Indole-3-acetaidoxime is the Metabolic Branch Point Between IAA and Indole Glucosinolate Biosynthesis Tryptophan-derived indole-3-acetaldoxime is also an intermediate in the biosynthesis of indole glucosinolates. Accordingly, seedlings of rnt1-1 contained reduced levels of indole glucosinolates compared to wild type seedlings whereas the molecularly complemented line 3.25.11 and the overexpression line 1.4.7 contained elevated levels of indole glucosinolates (FIG. 6). Wild type seedlings germinated on MS media supplemented with 100 $\mu$M of the CYP83B1 inhibitor tryptamine contained reduced levels of indole glucosinolates. This demonstrates that enzymes in glucosinolate and IAA biosynthesis utilize the same indole-3-acetaidoxime pool.

Example 5

IAN is not a Direct Product of indole-3-acetaldoxime Metabolism in IAA Biosynthesis IAN has been proposed to be the product of an indole-3-acetaldoxime metabolizing enzyme in IAA biosynthesis (e.g. Normanly and Bartel (1999) *Curr. Opin. Plant Biol.* 2:207–213). Accordingly, wild type *Arabidopsis* seedlings grown on media supplemented with 50 $\mu$M IAN phenocopy rnt1-1 seedlings by showing exfoliation at the root hypocotyl junction, the development of adventitious lateral root primordia on the hypocotyl and epinastic cotyledons (Normanly et al. (1997) *Plant Cell* 9:1781–1790 and our unpublished results). The observation that rnt1-1 seedling growth on 50 $\mu$M IAN (i) enhances the IAA phenotype of rnt1-l by almost completely inhibiting germination and (ii) exacerbates the primary/lateral root imbalance, further supports the involvement of IAN in IAA biosynthesis. Four nitrilases, differentially expressed during development and in response to environmental cues, catalyze hydrolysis of IAN to IAA in *Arabidopsis* (Bartel and Fink (1994) *Proc. Natl. Acad. Sci. USA* 91:6649–6653). The nitl mutant is insensitive to the auxin effects of exogenously applied LAN at the seedling stage (Normanly et al. (1997) *Plant Cell* 9:1781–1790). In accordance with the observed insensitivity of nit1 seedlings to IAN, NIT1 is most strongly expressed in the hypocotyl near the junction with the root in young seedlings as well as in the cotyledons. In contrast, NIT2 and NIT3 are expressed primarily in the cotyledons and NIT4 is expressed in the root tip (Bartel and Fink (1994) *Proc. Natl. Acad. Sci. USA* 91:6649–6653). If IAN is a direct metabolite of indole-3-acetaldoxime in IAA biosynthesis, then the rnt1-1 phenotype should be suppressed in the nit1 background. Surprisingly, the rnt1-1 phenotype is not suppressed in the nit1-1 background. This strongly suggests that LAN is not a direct metabolite of indole-3-acetaldoxime in IAA biosynthesis.

TABLE 1

Morphometric analysis of wild type (7.5 weeks of age) and rnt1-1 plants (18 weeks) grown in soil. Plants were analyzed at the same developmental stage.

| | Wild type | rnt1-1 |
|---|---|---|
| time of bolting | ~1 month | ~2 months |
| plant height | 35.1 ± 0.60 cm (n = 16) | 17.65 ± 1.63 cm (n = 20) |
| number of inflorescences | 3.28 ± 0.30 (n = 15) | 1.125 ± 0.07 (n = 24) |
| number of rosette leaves | 7.45 ± 0.28 (n = 11) | 26.1 ± 2.4 (n = 10) |
| rosette leaf width | 1.47 ± 0.05 cm (n = 15) | 0.69 ± 0.02 cm (n = 40) |
| rosette leaf length | 2.93 ± 0.15 cm (n = 16) | 1.40 ± 0.50 cm (n = 44) |
| pedicel length | 1.01 ± 0.02 cm (n = 21) | 0.75 ± 0.02 cm (n = 19) |
| distance between siliques on main inflorescence | 1.01 ± 0.11 cm (n = 20) | 0.76 ± 0.05 cm (n = 31) |

Example 6

Analysis of CYP83B1 Promoter Region

As described herein, a 5.5 Kb genomic fragment comprising the putative CYP83B1 promoter is sufficient to achieve molecular complementation of rnt1-1. We analyzed in silico 2.5 Kb upstream of the start codon of CYP83B1 for cis-acting elements (Higo et al. (1999) *Nucleic Acids Research* 27:297–300), and identified four putative AuxREs (auxin-responsive cis-acting elements; Guilfoyle et al. (1998) *Plant Physiol.* 118:341–347; Uhnasov et al. (1999) *Plant J.* 19:309–319).

Discussion

The inventors have shown herein that CYP83B1 is a regulator of auxin production in *Arabidopsis* by controlling the flux of indole-3-acetaidoxime into IAA and indole glucosinolate biosynthesis. In addition the inventors have shown that CYP83B1 catalyzes the first committed step in indole glucosinolate biosynthesis by metabolizing indole-3-acetaldoxime to its S-alkylthiohydroximate. The allelism of sur2 and CYP83B1 explains the strong auxin phenotype of the rnt1-1 mutant which is a knockout and therefore likely a null for CYP83B1. Elevated free auxin levels were measured in the sur2 mutant. In contrast to rnt1-1 in which the CYP83B1 gene is disrupted by insertion of a T-DNA, the CYP83B1 gene in sur2 likely is not completely inactivated, and therefore causes a less severe phenotype. In accordance with the observed phenotypes of sur2/rnt1-1, CYP83B1 is expressed in all tissues, with the highest expression level observed in the roots (Mizutani et al. (1998) *Plant Mol. Biol.* 37:39–52; Wenying Xu and our unpublished results).

Oximes are unstable compounds that do not accumulate in the cell. The low Ks and Km of CYP83B1 for indole-3-acetaldoxime would prevent accumulation of indole-3-acetaldoxime. In the CYP83B1 knock-out plants, the indole-3-acetaldoxime in excess is channeled into IAA biosynthesis leading to elevated IAA levels and thus increased apical dominance and reduced indole glucosinolate levels. Conversely, overexpression of CYP83B1 in *Arabidopsis* leads to a reduced IAA phenotype and loss of apical dominance and elevated indole glucosinolate levels, indicating that increased indole-3-acetaldoxime-oxidation results in a net loss of IAA.

Glucosinolate Biosynthesis

The above examples show that CYP83B1 catalyzes the formation of indole-3-acetaldoxime-N-oxide that forms an adduct with a nucleophile in vitro. Based on precursor feeding studies, cysteine, but not 1-thio-β-D-glucose has been proposed to be the sulfur donor in vivo (Wetter and Chrisom (1968) *Can. J. Biochem.* 46:931–935). Indole-3-acetaldoxime-N-oxide produced by CYP83B1 in vitro can form an adduct with cellular nucleophilic substrates such as glutathione, cysteine, and 1-thio-β-D-glucose, but the preferred thiol donor in vivo is unknown. The S-alkyl-thiohydroximate formed by CYP83B1 catalysis can be cleaved by a C-S lyase to generate thiohydroximates. It is well established that thiohydroximates are glucosylated by a soluble UDPG:thiohydroximate glucosyltransferase to form desulfoglucosinolates that are subsequently sulfated by a soluble PAPS transferase (reviewed by Halkier and Du (1997) *Trends Plant Sci.* 11:425–430).

*Arabidopsis* contains at least 23 different glucosinolates derived from tryptophan and from chain-elongated homologs of phenylalanine and methionine (Hogge et al., 1988). In *Arabidopsis* at least 6 related members for the CYP79 family have been identified. These enzymes probably all catalyze the conversion of amino acid and chain-elongated amino acids to their acetaldoximes (Bak et al. (1998) *Plant Mol. Biol.* 38:725–734; Hull et al. (2000) *Proc. Natl. Acad. Sci. USA* 97:307–317). The reduction of indole glucosinolate levels by only 50% in rnt1-1 suggests the presence of a functional homolog that partially complements CYP83B1. CYP83A1 may thus be a functional homology of CYP83B1 and may also metabolize indole-3-acetaldoxime to some degree. For a detailed discussion of CYP83A1, see copending, commonly owned application entitled "Methods of Modulating Glucosinolate Production in Plants" U.S. application Ser. No. 10/146,377, filed May 13, 2002, which is a continuation of Ser. No. 10/026,666, filed Dec. 18, 2001, abandoned), which application is incorporated herein by reference in its entirety.

The Role of IAN in IAA Biosynthesis

The auxin effects of IAN when supplemented to *Arabidopsis* are well documented. The results of IAN treatment of wild type and rnt1-1 mutant plants confirms that IAN can serve as a precursor in IAA biosynthesis. However, the inability of nit1-1 (which is resistant to exogenous IAN) to suppress the auxin phenotype of rnt1-1 indicates that LAN may not be the direct product of indole-3-acetaidoxime metabolism in IAA biosynthesis as often suggested. The role of IAN in IAA biosynthesis appears to be restricted to glucosinolate-producing species as they contain myrosinases that hydrolyze indole glucosinolates to IAN as well as nitrilases that can convert IAN to IAA (Thimann and Mahadevan (1964) *Arch. Biochem. Biophys.* 105:133). Apart from their function as bioactive natural products, indole glucosinolates may thus have a role in IAA biosynthesis as a sink for indole-3-acetaldoxime as well as a source of the IAA precursor IAN by turnover of the indole glucosinolate pool (FIG. 7), much in the same way as hydrolyzable IAA conjugates (Normanly and Bartel (1999) *Curr. Opin. Plant Biol.* 2:207–213). The level of IAN is two orders of magnitude higher than IAA in 7 day old seedlings (Normanly et al. (1997) *Plant Cell* 9:1781–1790) and the Km values for IAN hydrolysis by NIT1 and NIT2 are in the mM range (Battling et al., 1994). This is unexpected for an intermediate in a highly regulated biosynthetic pathway. Also, the observation that the isotope enrichment of IAN is lower than for IAA when radiolabeled tryptophan is administered to either *Arabidopsis* roots or shoots (Normanly et al. (1993) *Proc. Natl. Acad. Sci. USA* 90:10355–10359; Müller et al. (1998) *Planta.* 206:362–369-863), also indicate that IAN may not be a direct product of indole-3-acetaldoxime metabolism in IAA biosynthesis. Ectopic overexpression of the nitrilases does not give rise to an apparent IAA phenotype under normal conditions (Normanly et al. (1997) *Plant Cell* 9:1781–1790; Grsic et al. (1998) *J. Plant Physiol.* 153: 446–456).

In addition to indole-3-acetonitrile, indole-3-acetaldehyde has also been suggested to be a precursor of IAA biosynthesis derived from indole-3-acetaldoxime or indole-3-pyravic acid. Labeling studies have shown that indole-3-acetaldoxime can be converted to IAA with indole-3-acetaldehyde as an intermediate in higher plants (Rajapogal and Larsen (1972) *Planta* 103:45–54). Accordingly, it has been shown that in the IAA overproducer, sur1, the aldehyde oxidase activity is increased (Seo et al. (1998) *Plant Physiol.* 116:686–693). As opposed to the nitrilases, oxidases that catalyze conversion of indole-3-acetaidehyde to IAA are widespread in higher plants. This suggests that indole-3-acetaldehyde may be the intermediate in IAA biosynthesis from indole-3-acetaldoxime.

Tryptamine Inhibits Biosynthesis of Indole Glucosinolates.

Tryptamine was identified in the present study as an inhibitor of CYP83B1. This suggests that tryptamine may act as a regulator of the flux through the indole-3-acetaldoxime pathway to IAA. Expression of tryptophan decarboxylase, TDC, from *Catharanthus roseus* in *Brassica napus*, leads to an accumulation of tryptamine whereas the level of indole glucosinolates in leaves was reduced (Chavadej et al. (1994) *Proc. Natl. Acad. Sci. USA* 91:2166–2170). This was interpreted as a redirection of tryptophan into tryptamine rather than into indole glucosinolates. Based on the fact that tryptamine inhibits the enzymatic reaction catalyzed by CYP83B1 and thereby the production of precursors for indole glucosinolates, the role of tryptamine decarboxylase expression in *Brassica napus* should be reevaluated. Compared to expression in e.g. tobacco (Songstad et al. (1989) *Plant Physiol.* 94:1410–1413), the *Brassica napus* transgenic plants accumulated only 2% of the tryptamine levels found in transgenic tobacco. Tobacco does not produce indole glucosinolates and thus probably does not have a CYP83B I functional homolog. Therefore, expression of high levels of tryptamine in glucosinolate producing plants may be deleterious to the regeneration of transgenic lines due to elevated IAA levels. This implies that tryptamine may not necessarily be a general regulator of IAA biosynthesis.

Has Glucosinolate Biosynthesis Evolved from an IAA Biosynthetic Pathway?

Plants produce a vast array of natural products, often referred to as secondary metabolites, to accommodate their biotic and abiotic environment. These natural products are produced at a high expense of energy with natural selection as a driving force. Little is known about the evolutionary origin of the biosynthetic pathways behind these versatile compounds. Identification of the cytochrome P450 CYP83B1 as being involved in the regulation of IAA levels as well as in glucosinolate biosynthesis suggests that the glucosinolate biosynthetic pathway may have evolved from an IAA biosynthetic pathway.

The first step in IAA and glucosinolate biosynthesis is catalyzed by cytochromes P450 of the CYP79B subfamily (FIG. 7) (Hull et al. (2000) *Proc. Natl. Acad. Sci. USA* 97:2379–2384). CYP79 family members also catalyze the conversion of amino acids to their corresponding aldoximes in the biosynthesis of cyanogenic glucosides (Halkier et al. (1995) *Arch. Biochem. Biophys.* 322:369–377; Andersen et al. (2000) *J. Biol. Chem.* 275:1966–1977; Nielsen and Møller (2000) *Plant Physiol.* 122:307–317) and glucosinolates (Hull et al. (2000) *Proc. Natl. Acad. Sci. USA* 97:2379–2384, Wittstock and Halkier (2000) *J. Biol. Chem.* 275:14659–14666). In contrast to glucosinolates that are primarily found in the order Capparales, cyanogenic glucosides are widespread in nature and represent an evolutionary ancient trait. The oxime-metabolizing step in biosynthesis of the tyrosine-derived cyanogenic glucoside dhurrin is catalyzed by the cytochrome P450 CYP71E1 (Bak et al. (1998) *Plant Mol. Biol.* 36:393–405). A phylogenetic analysis of the cytochrome P450 supergene family revealed that CYP83B1 belongs to the larger CYP71 lade (Paquette et al. (2000) *DNA Cell Biol.* 19:307–317). It has often been suggested that glucosinolate biosynthesis has evolved from a cyanogenic predisposition (e.g. Poulton and Møller (1993) *Meth. Plant Biochem.* 9:209–237). The present finding of indole-3-acetaldoxime as a metabolic branch point in IAA and indole glucosinolate biosynthesis implies that the biosynthetic pathways of glucosinolates and cyanogenic glucosides have evolved from an existing IAA biosynthetic pathway, and that glucosinolates may not necessarily have evolved from a cyanogenic glucoside pathway.

Cytochromes P450 are heme thiolate enzymes anchored in the ER membrane that comprise one of the functionally most versatile supergene families. They are the catalysts of many complex steps in biosynthetic pathways. Currently 237 P450 genes distributed over 43 families have been identified in the genome of the model plant *Arabidopsis thaliana*. The CYP71 clade is the most expanded cytochrome P450 subfamily, as currently 45 members of the CYP71 family have been identified in *Arabidopsis*. The significance of the CYP71 lade in the recruitment of enzymes of indole and oxime metabolism is illustrated also by the four CYP71C P450s involved in biosynthesis of indole-derived defense compounds DIBOA and DIMBOA in grasses (Frey et al. (1997) *Science* 277:696–699) and by the involvement of CYP71B15 in biosynthesis of the indole-derived phytoalexin camalexin (Zhou et al. (2000) *Plant Cell* 11:2419–2428).

Overexpression of CYP79B2 and CYP79B3, recently shown to catalyze indole-3-acetaldoxime formation from tryptophan, did not lead to an IAA phenotype (Hull et al. (2000) *Proc. Natl. Acad. Sci. USA* 97:2379–2384). Similarly, overexpression of either of the four nitrilases in *Arabidopsis* did not lead to an IAA phenotype under normal conditions (Normanly et al. (1997) *Plant Cell* 9:1781–1790; Grsic et al. (1998) *J Plant Physiol.* 153:446–456; Grsic-Rausch et al. (2000) *Plant Physiol.* 122:369–378). CYP83B1 is thus the first enzyme demonstrated to regulate auxin production from tryptophan in *Arabidopsis*.

The invention claimed is:

1. A *Brassica* plant transformed with an exogenous polynucleotide encoding a polypeptide having the amino acid sequence set forth in SEQ ID NO:2.

2. The plant of claim 1, further comprising a control element operably linked to the exogenous polynucleotide.

3. A method of producing a transgenic *Brassica* plant said method comprising:
   (a) introducing an expression construct that comprises a polynucleotide encoding a polypeptide having the amino acid sequence set forth in SEQ ID NO:2 operably linked to a promoter which is capable of expressing the polypeptide into a *Brassica* plant cell to produce a transformed *Brassica* plant cell; and
   (b) producing a transgenic *Brassica* plant from the transformed plant cell.

4. The method of claim 3, wherein the polynucleotide is operably linked to a promoter selected from the group consisting of a tissue-specific promoter, an inducible promoter and a constitutive promoter.

5. The plant of claim 2, wherein the control element is a tissue-specific promoter.

6. The plant of claim 2, wherein the control is an inducible promoter.

7. The plant of claim 2, wherein the control element is a constitutive promoter.

* * * * *

SEQUENCE LISTING

<160> NUMBER OF SEQ ID NOS: 2

<210> SEQ ID NO 1
<211> LENGTH: 1663
<212> TYPE: DNA
<213> ORGANISM: Artificial Sequence
<220> FEATURE:
<223> OTHER INFORMATION: Description of Artificial Sequence: native CYP83B1

<400> SEQUENCE: 1

```
gtcaaacaga aaaaaatgga tctcttattg attatagccg gtttagtagc ggctgcagcc      60
ttcttttttcc tccgtagcac gaccaagaaa tctctccggt tacctccggg accaaaaggt    120
cttcctatta taggaaacct tcaccagatg gagaaattca accccaaca cttccttttc     180
cgtctctcca agctatacgg cccgattttc acgatgaaaa tcggtggccg tcgcctcgcg    240
gtgatctcct cggccgagct agccaaggag ctactcaaaa ctcaagacct caacttcacc    300
gctcgtcctc tcttgaaagg gcaacaaacc atgtcgtatc aaggccgtga gcttggtttc    360
ggacagtaca ccgcgtacta ccgtgagatg aggaagatgt gtatggtgaa cctcttcagc    420
ccgaaccgtg tcgcaagttt cagaccggtt agagaagaag agtgtcaacg gatgatggac    480
aagatctata aagccgctga tcaatcaggc accgttgatc taagtgagct tctcttgtct    540
ttcactaact gtgtcgtatg tagacaagct tttgggaaac ggtacaatga gtacggcaca    600
gagatgaaga gattcataga tatccttgtac gagacgcaag cacttttggg cactctgttt    660
ttctccgacc ttttcccctta tttcggattc cttgacaacc tcactggtct cagtgcacgt    720
ctcaagaaag ctttcaagga gcttgacact taccttcaag aacttctaga cgagactctt    780
gaccctaacc gccctaaaca agaaacagag agtttcattg atcttttgat gcagatctac    840
aaagaccaac ctttctccat caaattcact cacgaaaatg tcaaggccat gatattggat    900
attgttgtgc cgggaactga cacggcggct gcagtggtgg tatgggccat gacttacctt    960
attaagtacc ctgaagcaat gaagaaagct caagacgaag tgaggagtgt gataggtgac   1020
aaaggatatg tctctgaaga agacatacct aatctcccct acctaaaggc agtcatcaag   1080
gagtctcttc ggctcgaacc agtcatcccc attcttctac acagagaaac tatcgcagac   1140
gcaaagatag gtggctatga tattccggcc aagaccatca ttcaggtgaa cgcatgggcg   1200
gtttctcgtg acacagccgc gtggggagac aaccctaatg agttcattcc agagaggttc   1260
atgaacgagc acaaaggagt ggacttcaag ggccaagatt ttgagctcct accttttcggg   1320
tcgggccgga gaatgtgccc ggccatgcat cttgggattg caatggtaga gatacctttc   1380
gctaaccttc tctacaaatt tgactggagt ctacctaaag ggattaaacc agaggatata   1440
aagatggacg tcatgactgg actcgctatg cacaagaaag aacacctcgt tcttgcacca   1500
acgaaacaca tctgatgcta tatatatcat taggacgttt ctgctggtag atatggcgtg   1560
accaatggtt attttttcatt gcaatatccc ttttttgtttt aatgagtact atgttctcat   1620
tttaacgaat aaaaatgtat cagtgctctt gtttttggac tag                     1663
```

<210> SEQ ID NO 2
<211> LENGTH: 499
<212> TYPE: PRT
<213> ORGANISM: Artificial Sequence
<220> FEATURE:
<223> OTHER INFORMATION: Description of Artificial Sequence: native CYP83B1

<400> SEQUENCE: 2

```
Met Asp Leu Leu Leu Ile Ile Ala Gly Leu Val Ala Ala Ala Phe
 1               5                  10                  15

Phe Phe Leu Arg Ser Thr Thr Lys Lys Ser Leu Arg Leu Pro Pro Gly
                 20                  25                  30

Pro Lys Gly Leu Pro Ile Ile Gly Asn Leu His Gln Met Glu Lys Phe
             35                  40                  45

Asn Pro Gln His Phe Leu Phe Arg Leu Ser Lys Leu Tyr Gly Pro Ile
         50                  55                  60

Phe Thr Met Lys Ile Gly Gly Arg Arg Leu Ala Val Ile Ser Ser Ala
 65                  70                  75                  80

Glu Leu Ala Lys Glu Leu Leu Lys Thr Gln Asp Leu Asn Phe Thr Ala
                 85                  90                  95

Arg Pro Leu Leu Lys Gly Gln Gln Thr Met Ser Tyr Gln Gly Arg Glu
                100                 105                 110

Leu Gly Phe Gly Gln Tyr Thr Ala Tyr Tyr Arg Glu Met Arg Lys Met
            115                 120                 125

Cys Met Val Asn Leu Phe Ser Pro Asn Arg Val Ala Ser Phe Arg Pro
130                 135                 140

Val Arg Glu Glu Glu Cys Gln Arg Met Met Asp Lys Ile Tyr Lys Ala
145                 150                 155                 160

Ala Asp Gln Ser Gly Thr Val Asp Leu Ser Glu Leu Leu Ser Phe
                165                 170                 175

Thr Asn Cys Val Val Cys Arg Gln Ala Phe Gly Lys Arg Tyr Asn Glu
                180                 185                 190

Tyr Gly Thr Glu Met Lys Arg Phe Ile Asp Ile Leu Tyr Glu Thr Gln
            195                 200                 205

Ala Leu Leu Gly Thr Leu Phe Phe Ser Asp Leu Phe Pro Tyr Phe Gly
210                 215                 220

Phe Leu Asp Asn Leu Thr Gly Leu Ser Ala Arg Leu Lys Lys Ala Phe
225                 230                 235                 240

Lys Glu Leu Asp Thr Tyr Leu Gln Glu Leu Leu Asp Glu Thr Leu Asp
                245                 250                 255

Pro Asn Arg Pro Lys Gln Glu Thr Glu Ser Phe Ile Asp Leu Leu Met
                260                 265                 270

Gln Ile Tyr Lys Asp Gln Pro Phe Ser Ile Lys Phe Thr His Glu Asn
            275                 280                 285

Val Lys Ala Met Ile Leu Asp Ile Val Val Pro Gly Thr Asp Thr Ala
290                 295                 300

Ala Ala Val Val Val Trp Ala Met Thr Tyr Leu Ile Lys Tyr Pro Glu
305                 310                 315                 320

Ala Met Lys Lys Ala Gln Asp Glu Val Arg Ser Val Ile Gly Asp Lys
                325                 330                 335

Gly Tyr Val Ser Glu Glu Asp Ile Pro Asn Leu Pro Tyr Leu Lys Ala
            340                 345                 350

Val Ile Lys Glu Ser Leu Arg Leu Glu Pro Val Ile Pro Ile Leu Leu
                355                 360                 365

His Arg Glu Thr Ile Ala Asp Ala Lys Ile Gly Gly Tyr Asp Ile Pro
            370                 375                 380

Ala Lys Thr Ile Ile Gln Val Asn Ala Trp Ala Val Ser Arg Asp Thr
385                 390                 395                 400

Ala Ala Trp Gly Asp Asn Pro Asn Glu Phe Ile Pro Glu Arg Phe Met
```

-continued

```
                        405                     410                     415
Asn Glu His Lys Gly Val Asp Phe Lys Gly Gln Asp Phe Glu Leu Leu
            420                     425                     430

Pro Phe Gly Ser Gly Arg Arg Met Cys Pro Ala Met His Leu Gly Ile
            435                     440                     445

Ala Met Val Glu Ile Pro Phe Ala Asn Leu Leu Tyr Lys Phe Asp Trp
        450                     455                     460

Ser Leu Pro Lys Gly Ile Lys Pro Glu Asp Ile Lys Met Asp Val Met
465                     470                     475                 480

Thr Gly Leu Ala Met His Lys Lys Glu His Leu Val Leu Ala Pro Thr
                485                     490                     495

Lys His Ile
```